US009735305B2

(12) United States Patent
Li et al.

(10) Patent No.: US 9,735,305 B2
(45) Date of Patent: Aug. 15, 2017

(54) MONOLITHICALLY INTEGRATED FLUORESCENCE ON-CHIP SENSOR

(71) Applicant: INTERNATIONAL BUSINESS MACHINES CORPORATION, Armonk, NY (US)

(72) Inventors: Ning Li, White Plains, NY (US); Devendra K. Sadana, Pleasantville, NY (US); William T. Spratt, Ossining, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 14/859,961

(22) Filed: Sep. 21, 2015

(65) Prior Publication Data
US 2017/0084775 A1     Mar. 23, 2017

(51) Int. Cl.
*G01N 21/64*    (2006.01)
*H01S 5/026*    (2006.01)
(Continued)

(52) U.S. Cl.
CPC ........ H01L 31/173 (2013.01); B01L 3/5027 (2013.01); B01L 3/502707 (2013.01);
(Continued)

(58) Field of Classification Search
CPC ............... B01L 3/5027–3/502769; G01N 21/64–21/6489; H01S 5/0262;
(Continued)

(56) References Cited

U.S. PATENT DOCUMENTS 5,978,401 A * 11/1999 Morgan ............... H01S 5/0262
                                                 372/50.21
6,469,785 B1 * 10/2002 Duveneck ........... G01N 21/648
                                                 356/244
(Continued)

FOREIGN PATENT DOCUMENTS

CN    103667012 A    3/2014
CN    103824813 A    5/2014
(Continued)

OTHER PUBLICATIONS

Kern, Alexander, et al. "Monolithic VCSEL-PIN photodiode integration for bidirectional optical data transmission." IEEE Journal of Selected Topics in Quantum Electronics 19.4 (2013): 6100313-6100313.*

(Continued)

*Primary Examiner* — Victor A Mandala
*Assistant Examiner* — Regan J Rundio
(74) *Attorney, Agent, or Firm* — Scully, Scott, Murphy & Presser, P.C.; Louis J. Percello, Esq.

(57) ABSTRACT

After sequentially forming a first multilayer structure comprising a first set of semiconductor layers suitable for formation of a photodetector, an etch stop layer and a second multilayer structure comprising a second set of semiconductor layers suitable for formation of a light source over a substrate, the second multilayer structure is patterned to form a light source in a first region of the substrate. A first trench is then formed extending through the etch stop layer and the first multilayer structure to separate the first multilayer structure into a first part located underneath the light source and a second part that defines a photodetector located in a second region of the substrate. Next, an interlevel dielectric (ILD) layer is formed over the light source, the photodetector and the substrate. A second trench that defines (Continued)

a microfluidic channel is formed within the ILD layer and above the photodetector.

10 Claims, 18 Drawing Sheets

(51) Int. Cl.

| | |
|---|---|
| H01L 31/0232 | (2014.01) |
| H01L 31/173 | (2006.01) |
| H01L 33/00 | (2010.01) |
| H01L 33/32 | (2010.01) |
| H01L 31/18 | (2006.01) |
| B01L 3/00 | (2006.01) |
| H01L 31/12 | (2006.01) |
| H01L 25/16 | (2006.01) |
| H01L 21/02 | (2006.01) |
| H01L 27/15 | (2006.01) |
| H01L 27/144 | (2006.01) |
| H01L 21/365 | (2006.01) |
| H01L 21/44 | (2006.01) |
| H01L 21/465 | (2006.01) |
| C12Q 1/68 | (2006.01) |

(52) U.S. Cl.
CPC ..... *G01N 21/645* (2013.01); *H01L 21/02392* (2013.01); *H01L 21/02395* (2013.01); *H01L 25/167* (2013.01); *H01L 27/1443* (2013.01); *H01L 27/15* (2013.01); *H01L 31/02327* (2013.01); *H01L 31/125* (2013.01); *H01L 31/184* (2013.01); *H01L 33/0075* (2013.01); *H01L 33/32* (2013.01); *H01S 5/0262* (2013.01); *H01S 5/0264* (2013.01); *C12Q 1/6872* (2013.01); *G01N 2021/6471* (2013.01)

(58) Field of Classification Search
CPC ...... H01S 5/0264; H01L 31/00–31/208; H01L 33/00–33/648; C12Q 1/6869–1/6874
See application file for complete search history.

(56) References Cited

U.S. PATENT DOCUMENTS

| | | | | |
|---|---|---|---|---|
| 6,608,360 | B2* | 8/2003 | Starikov | H01L 31/108 257/449 |
| 6,667,496 | B2* | 12/2003 | Furukawa | G02B 6/12004 257/79 |
| 6,881,979 | B2* | 4/2005 | Starikov | H01L 31/108 257/432 |
| 6,946,286 | B2* | 9/2005 | Howard | H01L 31/173 250/461.1 |
| 7,221,455 | B2* | 5/2007 | Chediak | G01N 21/05 250/458.1 |
| 7,489,401 | B2* | 2/2009 | Kamei | G01N 21/6428 356/417 |
| 7,504,665 | B2* | 3/2009 | Summers | H01L 31/107 257/436 |
| 7,604,981 | B1* | 10/2009 | Harris, Jr. | G01N 21/6454 422/50 |
| 7,768,650 | B2* | 8/2010 | Bazylenko | G01N 21/253 356/491 |
| 8,306,607 | B1* | 11/2012 | Levi | A61B 5/0071 600/473 |
| 8,467,428 | B2* | 6/2013 | Gerlach | H01S 5/0264 372/50.124 |
| 8,717,569 | B2 | 5/2014 | Lo et al. | |
| 8,848,194 | B2* | 9/2014 | Walters | G01N 21/55 356/445 |
| 8,926,906 | B2* | 1/2015 | Packirisamy | 422/82.05 |
| 9,136,258 | B1* | 9/2015 | Wang | H01L 31/173 |
| 2002/0074553 | A1 | 6/2002 | Starikov et al. | |
| 2006/0124829 | A1* | 6/2006 | Song | H01S 5/0262 250/214.1 |
| 2008/0277606 | A1* | 11/2008 | Wang | B01L 3/5027 250/581 |
| 2009/0072243 | A1* | 3/2009 | Suda | H01L 21/26506 257/77 |
| 2010/0291703 | A1 | 11/2010 | Meng et al. | |
| 2011/0262307 | A1* | 10/2011 | Packirisamy | G01N 21/05 422/82.08 |
| 2011/0312753 | A1 | 12/2011 | Azimi et al. | |
| 2012/0082413 | A1* | 4/2012 | Alameh | G02B 6/4249 385/24 |
| 2014/0209929 | A1* | 7/2014 | Suh | H01L 31/167 257/84 |
| 2014/0244217 | A1 | 8/2014 | Lo et al. | |
| 2015/0285998 | A1* | 10/2015 | Babakhani | G02B 6/13 438/27 |
| 2015/0374269 | A1* | 12/2015 | Lee | A61B 5/14556 436/69 |
| 2016/0011111 | A1* | 1/2016 | Stoll | G01N 21/645 250/459.1 |

FOREIGN PATENT DOCUMENTS

| | | |
|---|---|---|
| CN | 104101588 A | 10/2014 |
| CN | 203981589 U | 12/2014 |
| CN | 103667012 B | 3/2015 |

OTHER PUBLICATIONS

O'Sullivan, Thomas, et al. "Implantable semiconductor biosensor for continuous in vivo sensing of far-red fluorescent molecules." Optics express 18.12 (2010): 12513-12525.*
Thrush, Evan, et al. "Integrated bio-fluorescence sensor." Journal of Chromatography A 1013.1 (2003): 103-110.*
Dandin, Marc, Pamela Abshire, and Elisabeth Smela. "Optical filtering technologies for integrated fluorescence sensors." Lab on a Chip 7.8 (2007): 955-977.*
Thrush, Evan, et al. "Integrated semiconductor vertical-cavity surface-emitting lasers and PIN photodetectors for biomedical fluorescence sensing." IEEE Journal of Quantum Electronics 40.5 (2004): 491-498.*
Thrush, Evan P., et al. "Laser background characterization in a monolithically integrated bio-fluorescence sensor." Biomedical Optics 2004. International Society for Optics and Photonics, 2004.*

* cited by examiner

MONOLITHICALLY INTEGRATED FLUORESCENCE ON-CHIP SENSOR

BACKGROUND

The present application relates to semiconductor fabrication, and more particularly to monolithic integration of light sources, photodetectors, optical filters and microfluidic channels for fluorescence on-chip sensors.

Fluorescence sensing has been widely used in biosensing and medical diagnosis. However, since these applications typically require bulky lenses and cameras, the resulting sensing systems are bulky, and thus are not suitable for use in portable detection devices. There have been efforts to miniaturize the biosensing and medical diagnosis systems for portable, point-of-care, or even wearable applications. However, the fabrication of fluorescence-based sensing systems is challenging since such sensing systems require various optical components including light sources, photodetectors and optical filters, etc., and all of which are made of different materials and by different processes. Therefore, there remains a need to develop methods for monolithic integration of these optical components on a single chip for sensing applications.

SUMMARY

The present application provides methods for monolithic integration of light sources, photodetectors, optical filters and microfluidic channels on a single chip. After sequentially forming a first multilayer structure comprising a first set of semiconductor layers suitable for formation of a photodetector, an etch stop layer and a second multilayer structure comprising a second set of semiconductor layers suitable for formation of a light source over a substrate, the second multilayer structure is patterned to form a light source in a first region of the substrate. A first trench is then formed extending through the etch stop layer and the first multilayer structure to separate the first multilayer structure into a first part located underneath the light source and a second part that defines a photodetector located in a second region of the substrate. Next, an interlevel dielectric (ILD) layer is formed over the light source, the photodetector and the substrate. A second trench that defines a microfluidic channel is formed within the ILD layer and above the photodetector.

In one aspect of the present application, a monolithically integrated semiconductor structure is provided. The semiconductor structure includes a first semiconductor device located over a first part of a multilayer structure that is located over a first region of a substrate and a second semiconductor device including a second part of the multilayer structure located over a second region of the substrate. The second part of the multilayer structure is separated from the first part of the multilayer structure by a space. The semiconductor structure also includes an interlevel dielectric (ILD) layer located over the first semiconductor device, the second semiconductor device and the substrate and within the space between the first part of the multilayer structure and the second part of the multilayer structure and a microfluidic channel located within the ILD layer. The microfluidic channel is present above the second semiconductor device.

In another aspect of the present application, a method of forming a monolithically integrated semiconductor structure is provided. The method includes first forming, from bottom to top, a first multilayer structure of semiconductor layers, an etch stop layer, and a second multilayer structure of semiconductor layers over a substrate. The second multilayer structure is then patterned to provide a first semiconductor device located in a first region of the substrate. The patterning exposes a portion of the etch stop layer. Next, a first trench is formed extending through the etch stop layer and the first multilayer structure. The first trench separates the first multilayer structure into a first part located underneath the first semiconductor device and a second part located in a second region of the substrate. After forming an interlevel dielectric (ILD) layer over the second part of the first multilayer structure, the first semiconductor device, and the substrate, a second trench is formed within the ILD layer. The second trench is located above the second part of the first multilayer structure.

In yet another aspect of the present application, a monolithically integrated semiconductor structure is provided. The semiconductor structure includes a substrate of a first conductivity type, a light source located over a first region of the substrate, a first doped region of a second conductivity type that is opposite to the first conductivity type located within a second region of the substrate, and a second doped region of the second conductivity type located above the first doped region and within the second region of the substrate. The first doped region has a first dopant concentration and the second doped region has a second dopant concentration greater than the first dopant concentration. The semiconductor structure also includes a microfluidic channel located within an interlevel dielectric (ILD) layer that is present over the substrate, the light source and the second doped region. The trench has a sidewall facing an output facet of the light source and a bottom surface located above the second doped region.

DETAILED DESCRIPTION

Figure 1:
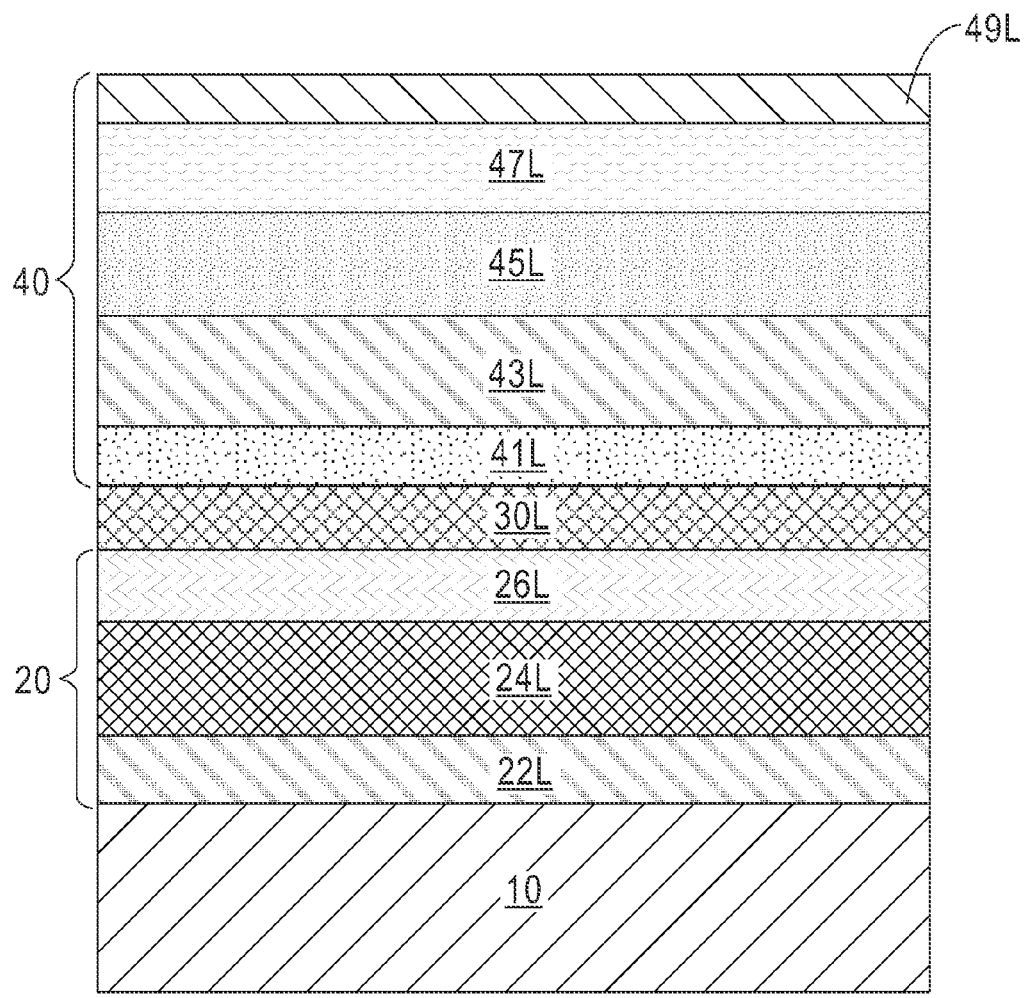
FIG. 1 is a cross-sectional view of a first exemplary semiconductor structure after sequentially forming a first multilayer structure, an etch stop layer and a second multilayer structure over a substrate according to a first embodiment of the present application.

The present application will now be described in greater detail by referring to the following discussion and drawings that accompany the present application. It is noted that the drawings of the present application are provided for illustrative purposes only and, as such, the drawings are not drawn to scale. It is also noted that like and corresponding elements are referred to by like reference numerals.

In the following description, numerous specific details are set forth, such as particular structures, components, materials, dimensions, processing steps and techniques, in order to provide an understanding of the various embodiments of the present application. However, it will be appreciated by one of ordinary skill in the art that the various embodiments of the present application may be practiced without these specific details. In other instances, well-known structures or processing steps have not been described in detail in order to avoid obscuring the present application.

Referring now to FIG. 1, a first exemplary semiconductor structure according to a first embodiment of the present application includes a substrate 10 and a first multilayer structure 20 and a second multilayer structure 40 formed thereon. An etch stop layer 30L is disposed between the first multilayer structure 20 and the second multilayer structure 40.

The substrate 10 may include a semiconductor material on which a compound semiconductor material can be epitaxially grown. Exemplary semiconductor materials that can be employed as the substrate 10 include, but are not limited to, Ge, SiGe, GaAs and InP. The thickness of the substrate 10 can be selected so as to be able to provide mechanical support to semiconductor devices to be formed thereupon. In one embodiment, the thickness of the substrate 10 can be from 50 µm to 2 mm, although lesser and greater thicknesses can also be employed.

The first multilayer structure 20 that is formed on the substrate 10 includes suitable semiconductor layers from which a photodetector can be formed. In one embodiment, the first multilayer structure 20 may include, from bottom to top, a doped bottom semiconductor layer 22L, a light-absorbing layer 24L and a doped top semiconductor layer 26L. In one embodiment, the doped bottom semiconductor layer 22L, the light-absorbing layer 24L and the doped top semiconductor layer 26L can be single crystalline, and can be formed utilizing an epitaxial growth (or deposition) process including molecular beam epitaxy (MBE) or metalorganic chemical vapor deposition (MOCVD). Each of the doped bottom semiconductor layer 22L, the light-absorbing layer 24L and the doped top semiconductor layer 26L thus formed can be epitaxially aligned among one another and with the substrate 10. By "epitaxially aligned" it is meant that the doped bottom semiconductor layer 22L, the light-absorbing layer 24L and the doped top semiconductor layer 26L have a same crystal orientation as that of the substrate 10. The dopants in the doped bottom semiconductor layer 22L and the doped top semiconductor 26L may be introduced by ion implantation, gas phase doping or by an in-situ doping process that is employed while the material of each of the doped bottom and the top semiconductor layers 22L and 26L is deposited.

The doped bottom semiconductor layer 22L may include an III-V compound semiconductor material containing a dopant of a first conductivity type (p-type or n-type). In one embodiment, the first conductivity type is n-type and the doped bottom semiconductor layer 22L includes a high concentration of an n-type dopant such as, for example, As or P. The dopant concentration of the first doped semiconductor layer 22L may range from $5 \times 10^{18}$ atoms/cm$^3$ to $1 \times 10^{21}$ atoms/cm$^3$. In one embodiment, the doped bottom semiconductor layer 22L is composed of n-doped AlGaAs.

The thickness of the doped bottom semiconductor layer 22L can be from 10 nm to 1 μm, although lesser and greater thicknesses can also be employed.

The light-absorbing layer 24L may include an intrinsic III-V compound semiconductor material. In one embodiment, the light-absorbing layer 24L is composed of GaAs. The light-absorbing layer 24L may have a thickness from 10 nm to 1 μm, although lesser and greater thicknesses can also be employed.

The doped top semiconductor layer 26L may include an III-V compound semiconductor material containing a dopant of a second conductivity type opposite the first conductivity type. In one embodiment, the second conductivity type is p-type and the second doped semiconductor layer 26L may comprise a high concentration of a p-type dopant such as, for example, B. The dopant concentration of the doped top semiconductor layer 26L may range from $5\times10^{18}$ atoms/cm$^3$ to $1\times10^{21}$ atoms/cm$^3$. The semiconductor material in the doped top semiconductor layer 26L may be the same as, or different from, that in the doped bottom semiconductor layer 22L. In one embodiment, the doped top semiconductor layer 26L includes a multilayer film formed by a p-doped AlGaAs layer and a p-doped GaAs layer overlying the p-doped AlGaAs layer. The doped top semiconductor layer 26L may have a thickness from 10 nm to 1 μm, although lesser and greater thicknesses can also be employed.

The etch stop layer 30L that is formed on the topmost surface of the first multilayer structure 20 (i.e., the top surface of the doped top semiconductor layer 26L) may be comprised of InGaP or InAlP. The etch stop layer 30L may be deposited utilizing MBE or MOCVD such that the etch stop layer 30L is epitaxially aligned with the doped top semiconductor layer 26L. The etch stop layer 30L may have a thickness from 10 nm to 50 nm, although lesser and greater thicknesses can also be employed.

The second multilayer structure 40 that is formed on the etch stop layer 30L includes suitable semiconductor layers from which a light source (e.g., a laser diode or a light-emitting diode) can be formed. In one embodiment, the second multilayer structure 40 may include, from bottom to top, a bottom contact layer 41L, a bottom cladding layer 43L, a light-emitting layer 45L, a top cladding layer 47L and a top contact layer 49L. The light-emitting layer 45L is a layer within which light is emitted by recombination of carriers. The bottom cladding layer 43L and the top cladding layer 47L are layers for increasing a carrier density in the light-emitting layer 45L. The semiconductor layers 41L, 43L, 45L, 47L, 49L in the second multilayer structure 40 may be deposited utilizing an epitaxial growth (or deposition) process including MBE or MOCVD so that the etch stop layer 30L, the bottom contact layer 41L, the bottom cladding layer 43L, the light-emitting layer 45L, the top cladding layer 47L and the top contact layer 49L are epitaxially aligned among one another.

The bottom contact layer 41L may include a first n-doped III-V compound semiconductor material and may have a thickness ranging from 100 nm to 500 nm, although lesser and greater thicknesses can also be employed. In one embodiment, the bottom contact layer 41L is made of Si doped GaAs having a dopant concentration of $3\times10^{18}$ atoms/cm$^3$ and a thickness of 500 nm.

The bottom cladding layer 43L may include a second n-doped III-V compound semiconductor material and may have a thickness ranging from 10 nm to 1 μm, although lesser and greater thicknesses can also be employed. In one embodiment, the bottom cladding layer 43L has a bilayer structure including a lower layer of Si doped $Al_xGa_{1-x}As$ with x=0.60 and an upper layer of Si doped AlGaAs. The lower layer has a dopant concentration of $5\times10^{17}$ atoms/cm$^3$ and a thickness of 200 nm, while the upper layer has a dopant concentration of $1\times10^{18}$ atoms/cm$^3$ and a thickness of 600 nm.

The light-emitting layer 45L may have a quantum well structure. In one embodiment, the light-emitting layer 45L includes a quantum well layer of a first III-V compound semiconductor material and barrier layers of a second III-V compound semiconductor material between which the quantum well layer is sandwiched. In one embodiment, the quantum well layer is composed of AlGaAs and the barrier layers are composed of $Al_xGa_{1-x}As$ with 0<x<1.

The top cladding layer 47L may include a first p-doped III-V compound semiconductor material and may have a thickness ranging from 10 nm to 1 μm, although lesser and greater thicknesses can also be employed. The III-V compound semiconductor material that provides the top cladding layer 47L may be the same as, or different from, that of the bottom cladding layer 43L. In one embodiment, the top cladding layer 47L has a bilayer structure including a lower layer of C doped AlGaAs and an upper layer of C doped $Al_xGa_{1-x}As$ with x=0.60. The lower layer has a dopant concentration of $5\times10^{17}$ atoms/cm$^3$ and a thickness of 600 nm, while the upper layer has a dopant concentration of $3\times10^{18}$ atoms/cm$^3$ and a thickness of 200 nm.

The top contact layer 49L may include a second p-doped III-V compound semiconductor material and may have a thickness ranging from 100 nm to 1 μm, although lesser and greater thicknesses can also be employed. The III-V compound semiconductor material that provides the top contact layer 49L may be the same as, or different from, that of the bottom contact layer 41L. In one embodiment, the top contact layer 49L is made of C doped GaAs having a dopant concentration of $3\times10^{18}$ atoms/cm$^3$ and a thickness of 200 nm.

Figure 2:
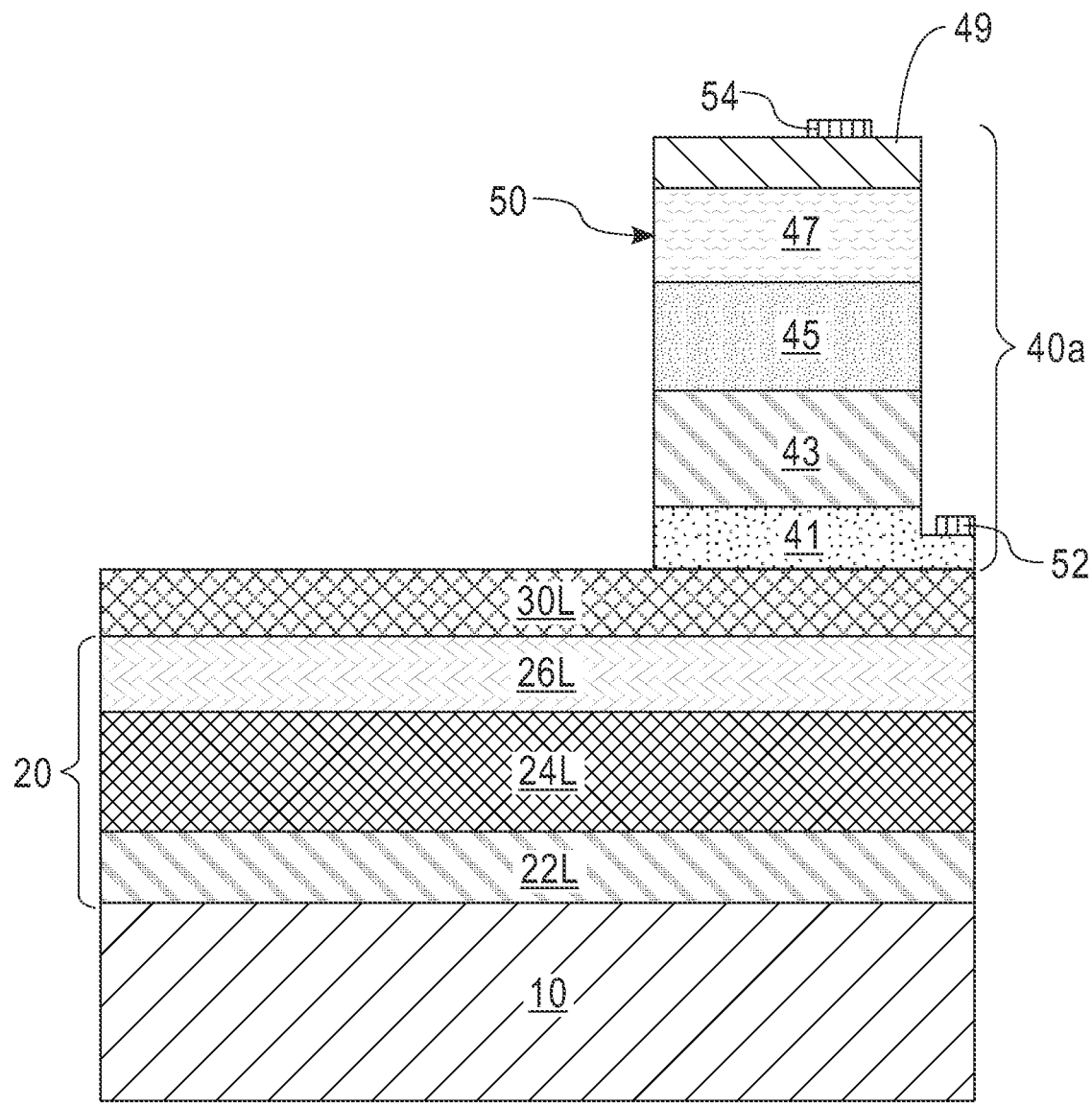
FIG. 2 a cross-sectional view of the first exemplary semiconductor structure of FIG. 1 after forming a light source over a portion of the first multilayer structure located in a first region of the substrate and forming contact structures that provide electrical connections to components of the light source.

Referring to FIG. 2, a light source 40a is formed on a portion of the first multilayer structure 20 located in a first region of the substrate 10 by patterning the second multilayer structure 40 utilizing conventional photolithography and etching techniques. A first photoresist layer (not shown) is applied over the topmost surface of the second multilayer structure 40 (i.e., the top surface of the top contact layer 49L) and lithographically patterned to provide a patterned first photoresist layer covering a portion of the second multilayer structure 40 form which the light source 40a is subsequently formed. The portion of the second multilayer structure 40 that is exposed by the patterned first photoresist layer is then removed by an anisotropic etch. The anisotropic etch can be a dry etch such as, for example, reactive ion etching (RIE) or a wet chemical etch. The patterning of the second multilayer structure 40 exposes a portion of the etch stop layer 30L. The patterned first photoresist layer is subsequently removed, for example, by ashing.

The remaining portion of the bottom contact layer 41L is herein referred to as a bottom contact portion 41, the remaining portion of the bottom cladding layer 43L is herein referred to as a bottom cladding portion 43, the remaining portion of the light-emitting layer 45L is herein referred to as the light-emitting portion 45. The remaining portion of the top cladding layer 47L is herein referred to as a top cladding portion 47. The remaining portion of the top contact layer 49L is herein referred to as a top contact portion 49. The bottom contact portion 41, the bottom cladding portion 43, the light-emitting portion 45, the top cladding portion 47 and the top contact portion 49 together constitute the light source 40a.

Next, the top contact portion 49, the top cladding portion 47, the light-emitting portion 45, the bottom cladding portion 43 and an upper portion of the bottom contact portion 41 are selectively etched to form a mesa structure, thus exposing an end portion of the bottom contact portion 41. The mesa etching can be performed by applying and lithographically patterning a second photoresist layer (not shown) that is formed over the etch stop layer 30L and light source 40a, and transferring the pattern in the patterned second photoresist layer through the top contact portion 49, the top cladding portion 47, the light-emitting portion 45 and the bottom cladding portion 43 and into the upper portion of the bottom contact portion 41 by a second anisotropic etch. The second anisotropic etch can be a dry etch such as RIE or a wet chemical etch. The patterned second photoresist layer is subsequently removed, for example, by ashing.

Subsequently, contact structures are formed on the bottom contact portion 41 and the top contact portion 49 by metallization processes. The contact structures includes a first contact structure 52 formed directly on an exposed end portion of the bottom contact portion 41 and a second contact structure 54 formed directly on a top surface of the top contact portion 49. The first contact structure 52 can be formed prior to formation of the second contact structure 54, or can be formed after formation of the second contact structure 54. The first contact structure 52 includes a first metal that forms ohmic contact with the bottom contact portion 41. Exemplary first metals include, but are not limited to, Al, Cu, or Ti/Au. The second contact structure 54 includes a second metal that forms ohmic contact with the top contact portion 49. Exemplary second metals include, but are not limited to, Pt/Ni/Au, Au/Ge/Ni, Al, or Cu. The first and second metals can be deposited by a directional deposition method which can be a vacuum evaporation or a collimated physical vapor deposition.

In the first embodiment of the present application, the light source 40a can be an edge-emitting laser diode or an edge-emitting light-emitting diode. In one embodiment, the light source 40a is an edge-emitting laser diode having an output facet 50 located at one end of the light source 40a. The output facet 50 comprises sidewalls of the top contact portion 49, the top cladding portion 47, the light-emitting portion 45, the bottom cladding portion 43 and the bottom contact layer 41 that are vertically coincident with one another. As used herein, a group of surfaces is "vertically coincident" with one another if there exists a vertical plane from which the group of surfaces does not deviate by more than three times the maximum surface roughness of the group of surfaces.

Figure 3:
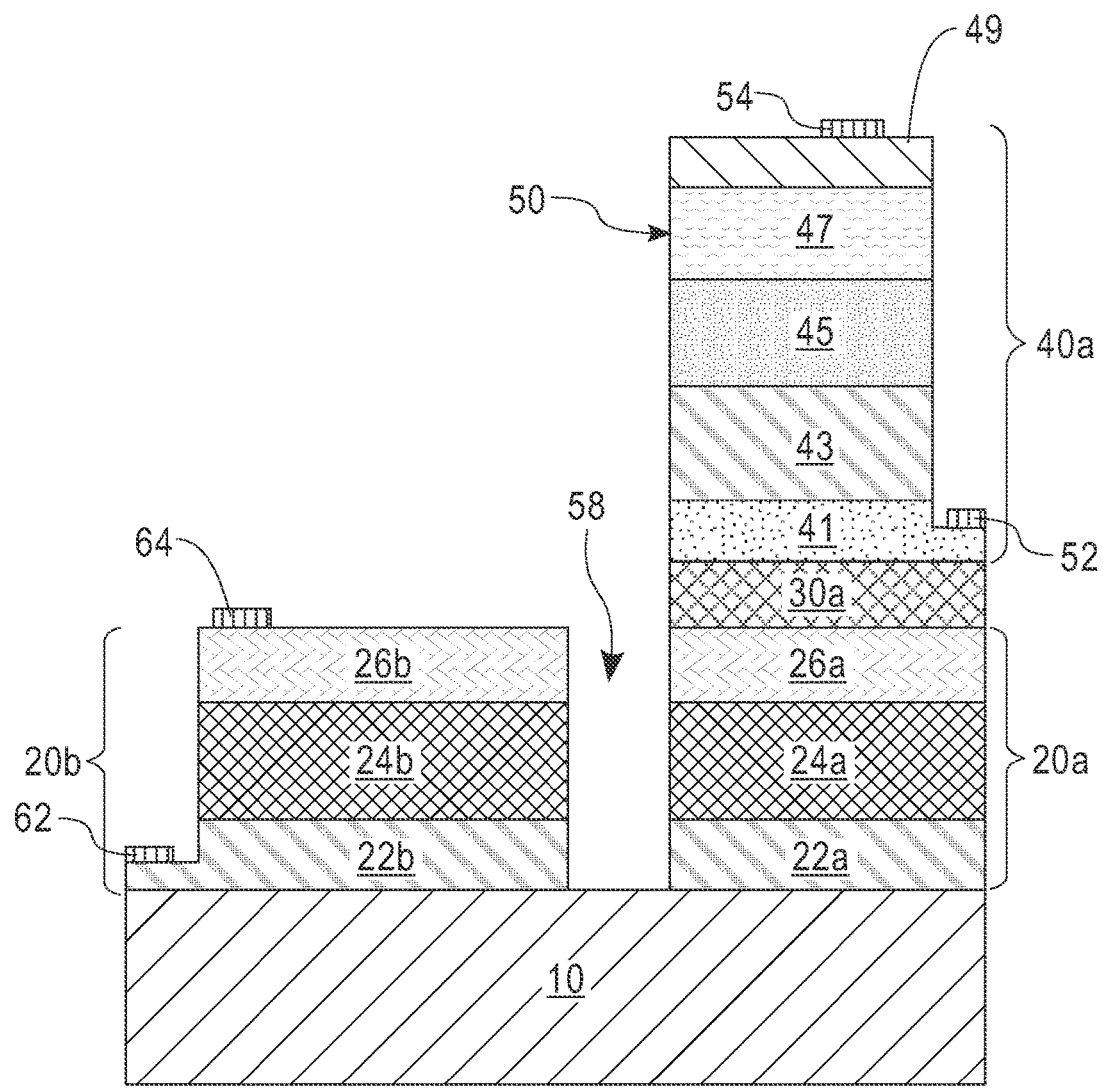
FIG. 3 is a cross-sectional view of the first exemplary semiconductor structure of FIG. 2 after forming a photodetector in a second region of the substrate and forming contact structures that provide electrical connections to components of the photodetector.

Referring to FIG. 3, a photodetector 20b is formed in a second region of the substrate 10 by patterning the first multilayer structure 20 utilizing conventional photolithography and etching techniques. A third photoresist layer (not shown) is applied over the etch stop layer 30L and the light source 40a and lithographically patterned to form an opening therein. The opening exposes a portion of the etch stop layer 30L and an underlying portion of the first multilayer structure 20 adjoined to the light source 40a. The pattern of the opening in the third photoresist layer is subsequently transferred into the etch stop layer 30L and the first multilayer structure 20 by a third anisotropic etch to form a trench 58 therein. The third anisotropic etch can be a dry etch such as RIE or a wet chemical etch. The patterned third photoresist layer is subsequently removed, for example, by ashing.

The trench 58 separates the first multilayer structure 20 into two parts. The first part of the first multilayer structure 20 is formed in the first region underneath the light source 40a and includes, from bottom to top, a first doped bottom semiconductor portion 22a which is a remaining portion of the doped bottom semiconductor layer 22L located in the first region of the substrate 10, a first light-absorbing portion 24a which is a remaining portion of the light-absorbing layer 24L located in the first region of the substrate 10 and a first doped top semiconductor portion 26a which is a remaining portion of the doped top semiconductor layer 26L located in the first region of the substrate 10. The second part of the first multilayer structure 20 is located in a second region of the substrate 10 and includes, from bottom to top, a second doped bottom semiconductor portion 22b which is a remaining portion of the doped bottom semiconductor layer 22L located in the second region of the substrate 10, a second light-absorbing portion 24b which is a remaining portion of the light-absorbing layer 24L located in the second region of the substrate 10 and a second doped top semiconductor portion 26b which is a remaining portion of the doped top semiconductor layer 26L located in the second region of the substrate 10. The first part of the first multilayer structure 20 in the first region is a non-device part 20a over which the light source 40a is located. The second part of the first multilayer structure 20 in the second region constitutes the photodiode 20b. The trench 58 also separates the etch stop layer 30L into two portions. The first portion of the etch stop layer 30L that is located between the light source 40a and the non-device part 20a of the first multilayer structure 20 is herein referred to as the first etch stop portion 30a. In one embodiment, a sidewall of the first etch stop portion 30a and sidewalls of the first doped bottom semiconductor portion 22a, the first light-absorbing portion 24a and the first doped top semiconductor portion 26a in the non-device portion 20a of the first multilayer structure 20 are vertically coincident with the output facet of the light source 40a. The second portion of the etch stop layer 30L is subsequently removed from the topmost surface of the photodetector 30b to expose the second doped top semiconductor layer portion 26b.

Subsequently, the second doped top semiconductor portion 26b, the second light-absorbing portion 24b and an upper portion of the second doped bottom semiconductor portion 22b are selectively etched to form a mesa structure, thus exposing an end portion of the second doped bottom semiconductor portion 22b. The mesa etching of the second doped top semiconductor portion 26b, the second light-absorbing portion 24b and the second doped bottom semiconductor portion 22b can be performed by applying and lithographically patterning a fourth photoresist layer (not shown) that is formed within the trench 58 and on the photodetector 20b and light source 40a and transferring the pattern in the patterned fourth photoresist layer through the second doped top semiconductor layer portion 26b and the second light-absorbing portion 24b and into the upper portion of the second doped bottom semiconductor portion 22b by a fourth anisotropic etch. The fourth anisotropic etch can be a dry etch such as RIE or a wet chemical etch. The patterned fourth photoresist layer is subsequently removed, for example, by ashing.

Subsequently, contact structures are formed on the second doped bottom semiconductor portion 22b and the second doped top semiconductor portion 26b by metallization processes. The contact structures include a third contact structure 62 formed directly on the exposed portion of the second doped bottom semiconductor portion 22b, and a fourth contact structure 64 formed directly on a top surface of the second doped top semiconductor portion 26b. The third contact structure 62 can be formed prior to formation of the fourth contact structure 64, or can be formed after formation of the fourth contact structure 64. The third contact structure 62 includes a third metal that forms ohmic contact with the second doped bottom semiconductor portion 22b. Exemplary third metals include, but are not limited to, Al, Cu or Ti/Au. The fourth contact structure 64 includes a fourth metal that forms ohmic contact with the second doped top semiconductor portion 26b. Exemplary second metals include, but are not limited to, Pt/Ni/Au, Au/Ge/Ni, Al, or Cu. The third and fourth metals can be deposited by a directional deposition method which can be a vacuum evaporation or collimated physical vapor deposition.

Figure 4:
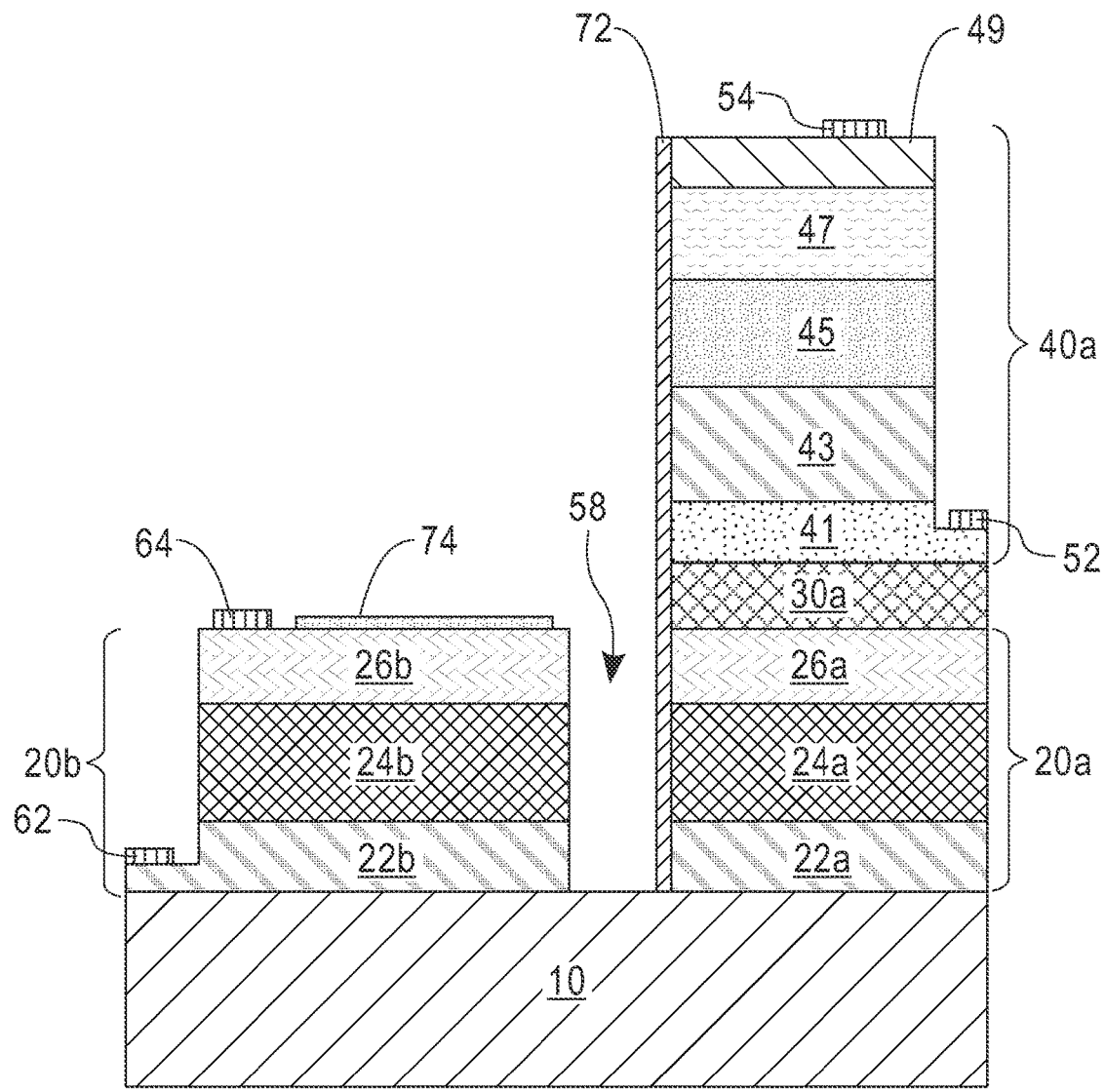
FIG. 4 is a cross-sectional view of the first exemplary semiconductor structure of FIG. 3 after forming a first optical filter on an output facet of the light source and forming a second optical filter on top of the photodetector.

Referring to FIG. 4, a first optical filter 72 is formed on the output facet (i.e., sidewalls of the bottom contact portion 41, the bottom cladding portion 43, the light-emitting portion 45, the top cladding portion 47 and the top contact portion 49) of the light source 40a and sidewalls of the first etch stop portion 30a and the first doped top semiconductor portion 26a, the first light-absorbing portion 24a and first doped bottom semiconductor portion 22a in the non-device part 20a. The first optical filter 72 may be an optical bandpass filter transmitting a specific wavelength range of light emitted from the light source 40a. The light emitted from the light source 40a is configured to excite fluorescence materials in an analyte to be detected in a microfluidic channel subsequently formed.

The first optical filter 72 may include a first multilayer coating. In one embodiment, the first multilayer coating includes alternating layers of a first coating layer having a high refractive index and a second coating layer having a low refractive index. For example, the first coating layer may have a refractive index of at least 1.85 and can be formed of SiN, HfO$_2$, TiN, Ta$_2$O$_5$ or TiO$_2$. The second coating layer may have a refractive index of less than 1.8 and can be formed of SiO$_2$, Al$_2$O$_3$ or SiON. The thicknesses and the number of the alternating first and second coating layers are configured to allow a specific wavelength range of light emitted from the light source 40a passing through. In one embodiment, the first coating layer may have a thickness from 15 nm to 50 nm and the second coating layer may have a thickness from 160 nm to 200 nm, although lesser and greater thicknesses can also be employed for each of the first coating layer and the second coating layer.

The first optical filter 72 may be formed by depositing the first multilayer coating on the exposed surfaces of the light source 40a, the non-device part 20a of the first multilayer structure 20, the first etch stop portion 30a and the substrate 10 by atomic layer deposition (ALD) while masking the photodetector 20b and removing portions of the first multilayer coating that are not present on the output facet of the light source 40a and the sidewalls of the non-device part 20a and the first etch stop portion 30a.

Next, a second optical filter 74 is formed on the top surface of the second doped top semiconductor portion 26b of the photodetector 20b. The second optical filter 74 is generally transmissive except in the specific wavelength range of the excitation light emitted from the light source 40a.

The second optical filter 74 may include a second multilayer coating. In one embodiment, the second multilayer coating includes alternating layers of a third coating layer having a high refractive index and a fourth coating layer having a low refractive index. For example, the third coating layer may be formed of a high refractive index material the same as, or different from that of the first coating layer. The fourth coating layer may be formed of a low refractive index material the same as, or different from that of the second coating layer. The thicknesses and the number of the alternating third and fourth coating layers are configured to allow the light emitted from the fluorescence materials in the analyte to be detected in the microfluidic channel passing through, while absorbing the specific wavelength range of light emitted from the light source 40a. In one embodiment, the third coating layer may have a thickness from 15 nm to 50 nm and the fourth coating layer may have a thickness from 160 nm to 200 nm, although lesser and greater thicknesses can also be employed for each of the third coating layer and the fourth coating layer.

The second optical filter 74 may be formed by depositing the second multilayer coating on the exposed surfaces of the photodetector 20b and substrate 10 by ALD while masking the first optical filter 72 and the light source 40a and removing portions of the second multilayer coating that are not present on the top surface of the second doped top semiconductor portion 26b in the photodetector 20b.

Figure 5:
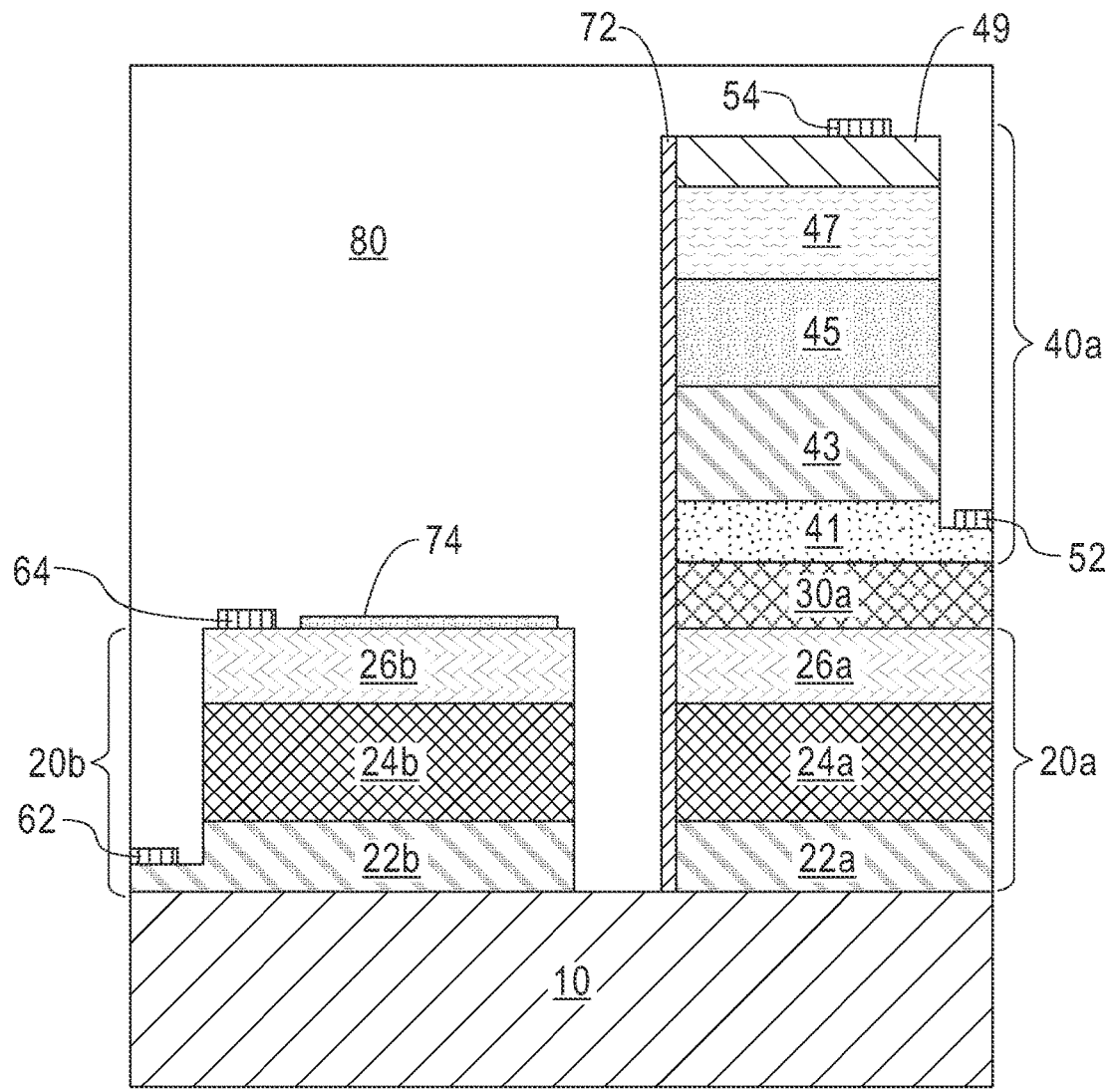
FIG. 5 is a cross-sectional view of the first exemplary semiconductor structure of FIG. 4 after forming an interlevel dielectric (ILD) layer over the light source, the photodetector and the substrate.

Referring to FIG. 5, an interlevel dielectric (ILD) layer 80 is deposited to cover the light source 40a and the photodetector 20b and to completely fill the trench 58. The ILD layer 80 may comprise any dielectric material including, for example, oxides, nitrides or oxynitrides. In one embodiment, the ILD layer 80 includes silicon dioxide. The ILD layer 80 may be formed, for example, by CVD or spin-coating. The ILD layer 80 may be self-planarizing, or the top surface of the ILD 80 can be planarized, for example, by chemical mechanical planarization (CMP). In one embodiment, the planarized top surface of the ILD layer 80 is located above the top surface of the second contact structure 54.

Figure 6:
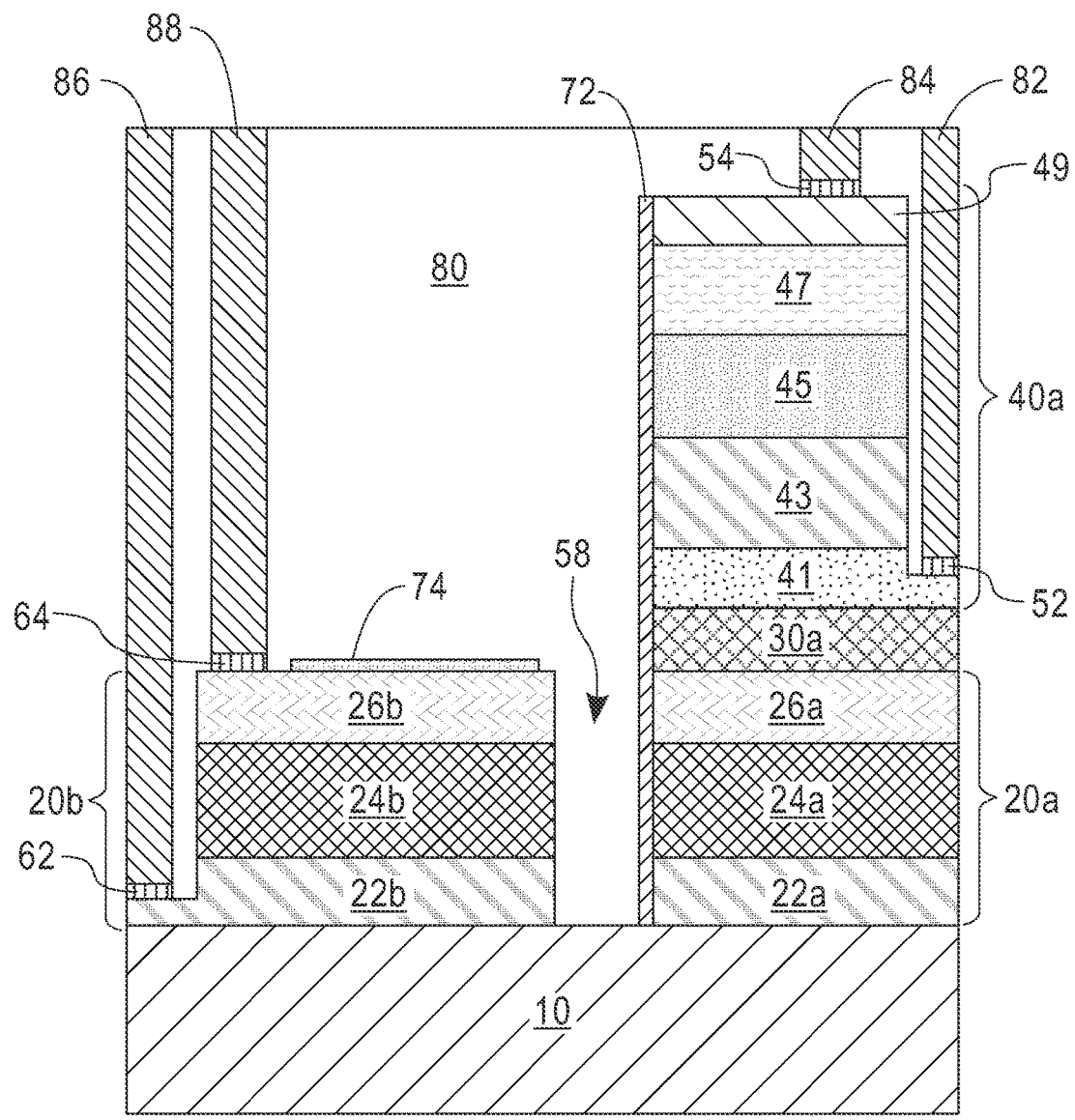
FIG. 6 is a cross-sectional view of the first exemplary semiconductor structure of FIG. 5 after forming interconnect structures electrically connected to contact structures in the light source and the photodetector.

Referring to FIG. 6, interconnect structures are formed through the ILD layer 80 to provide electrical contacts to various contact structures 52, 54, 62, 64 of the light source 40a and the photodetector 20b. The interconnect structures include a first interconnect structure 82 in contact with the first contact structure 52, a second interconnect structure 84 in contact with the second contact structure 54, a third interconnect structure 86 in contact with the third contact structure 62 and a fourth interconnect structure 88 in contact with the fourth contact structure 64. The interconnect structures 82, 84, 86, 88 may be formed by formation of interconnect contact openings (not shown) that extend through the ILD layer 80 by a combination of lithographic patterning and anisotropic etch followed by deposition of a conductive material (e.g., tungsten) and planarization that removes an excess portions of the conductive material from above the top surface of the ILD layer 80. Optionally, contact liners (not shown) may be formed on the sidewalls and bottoms surfaces of the interconnect contact openings before filling the interconnect contact openings with the conductive material. The contact liners may include TiN.

Figure 7:
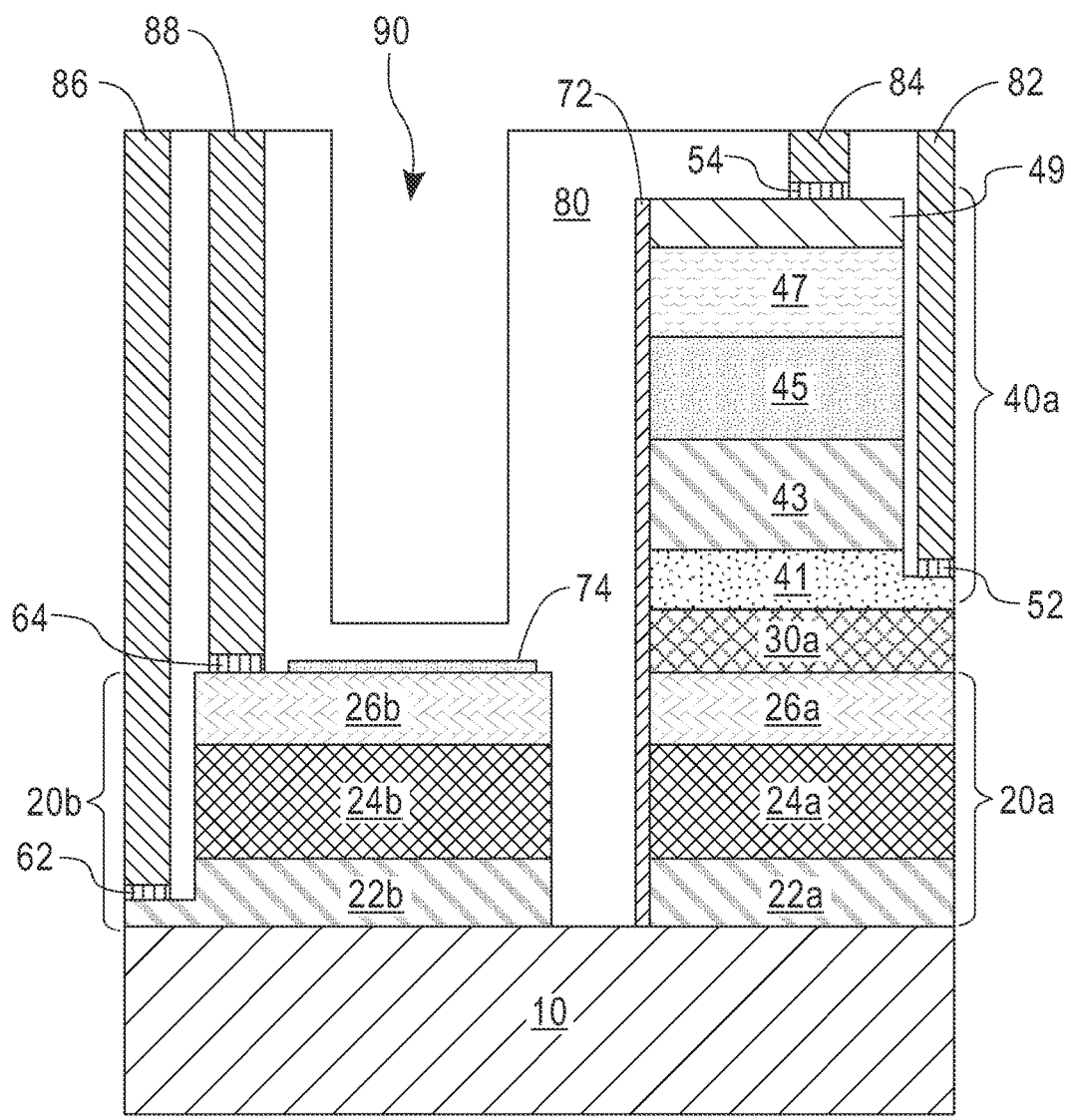
FIG. 7 is a cross-sectional view of the first exemplary semiconductor structure of FIG. 6 after forming a trench within the ILD layer.

Referring to FIG. 7, a second trench 90 is formed within the ILD layer 80. The second trench 90 may be formed by applying a mask layer (not shown) over the ILD layer 80 and the interconnect contact structures 82, 84, 86, 88 and lithographically patterning the mask layer to form an opening therein. The mask layer can be a photoresist layer or a photoresist layer in conjunction with hardmask layer(s). The pattern of the opening in the mask layer is then transferred into the ILD layer 80 by an anisotropic etch to form the second trench 90 within the ILD layer 80. The anisotropic etch can be a dry etch such as, for example, RIE or a wet chemical etch. The second trench 90 that is formed may have a width ranging from 3 µm to 500 µm and a depth ranging from 5 µm to 300 µm, although lesser and greater widths or depths can also be employed. Upon formation of the second trench 90, the patterned mask layer can be removed, for example, by oxygen-based plasma etching. The second trench 90 defines a microfluidic channel within which the presence of an analyte can be detected by the photodetector 20b. The second trench 90 is thus located above the second optical filter 74 so as to allow emission from fluorescence materials in the analyte passing through the second optical filter 74 and being detected by the photodetector 20b.

A first fluorescence on-chip sensor is thus formed by monolithically integrating a light source 40a which is an edge-emitting light source, a photodetector 20b and a microfluidic channel (i.e., second trench 90) on the same substrate 10. In the first embodiment of the present application, the light source 40a is an edge-emitting laser diode located on one side of the microfluidic channel that is located above the photodetector 20b. Thus in the first embodiment, the light source 40a and the photodetector 20b are arranged orthogonally to each other. This orthogonal configuration prevents direct illumination of the photodetector 20b by the light source 40a, and thus the sensor sensitivity can be increased. During operation, the light emitted from the output facet of the light source 40a passes through the first optical filter 72 and illuminates the fluorescence materials in the analyte present in the microfluidic channel (i.e., second trench 90). The generated fluorescence light goes through the second optical filter 74 and into the photodetector 20b, which in turn generates an electrical signal in response. This electrical signal is indicative of the amount of target molecules present in the analyte.

Figure 8:
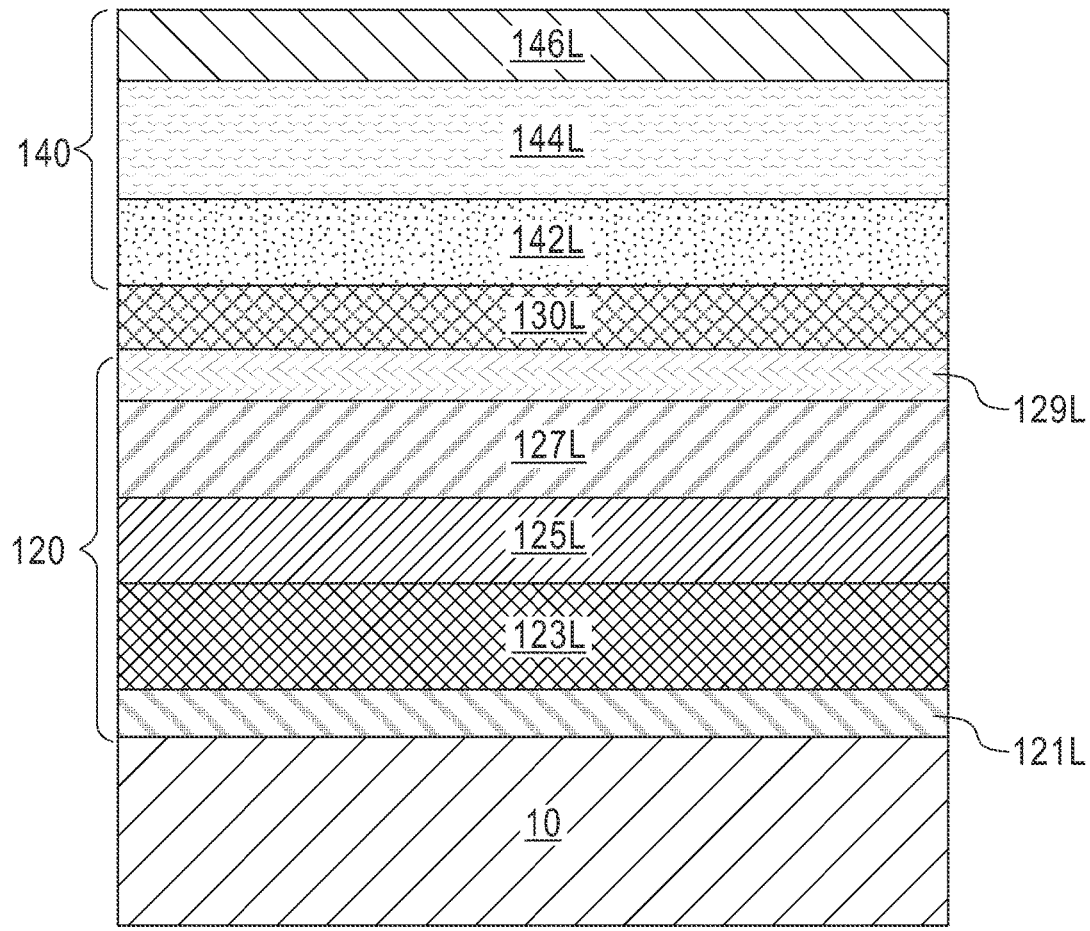
FIG. 8 is a cross-sectional view of a second exemplary semiconductor structure after sequentially forming a first multilayer structure, an etch stop layer and a second multilayer structure over a substrate according to a second embodiment of the present application.

Referring to FIG. 8, a second exemplary semiconductor structure of the present application according to a second embodiment of the present application includes a substrate 10 and a first multilayer structure 120 and a second multilayer structure 140 formed thereon. An etch stop layer 130L is disposed between the first multilayer structure 120 and the second multilayer structure 140.

Unlike the first embodiment, in the second embodiment, the first multilayer structure 120 includes suitable semiconductor layers from which a light source is formed, while the second multilayer structure 140 includes suitable semiconductor layers from which a photodetector is formed. For example, the first multilayer structure 120 may include, from bottom to top, a bottom contact layer 121L, a bottom cladding layer 123L, a light-emitting layer 125L, a top cladding layer 127L and a top contact layer 129L. The second multilayer structure 140 may include, from bottom to top, a doped bottom semiconductor layer 142L, a light-absorbing layer 144L and a doped top semiconductor layer 146L. In the second embodiment, each of the substrate 10, the etch stop layer 130L and semiconductor layers in the first multilayer structure 120 and the second multilayer structure 140 can have the same composition and thickness as those of a corresponding layer in the first embodiment, and can be formed by performing processing steps described above in FIG. 1.

Figure 9:
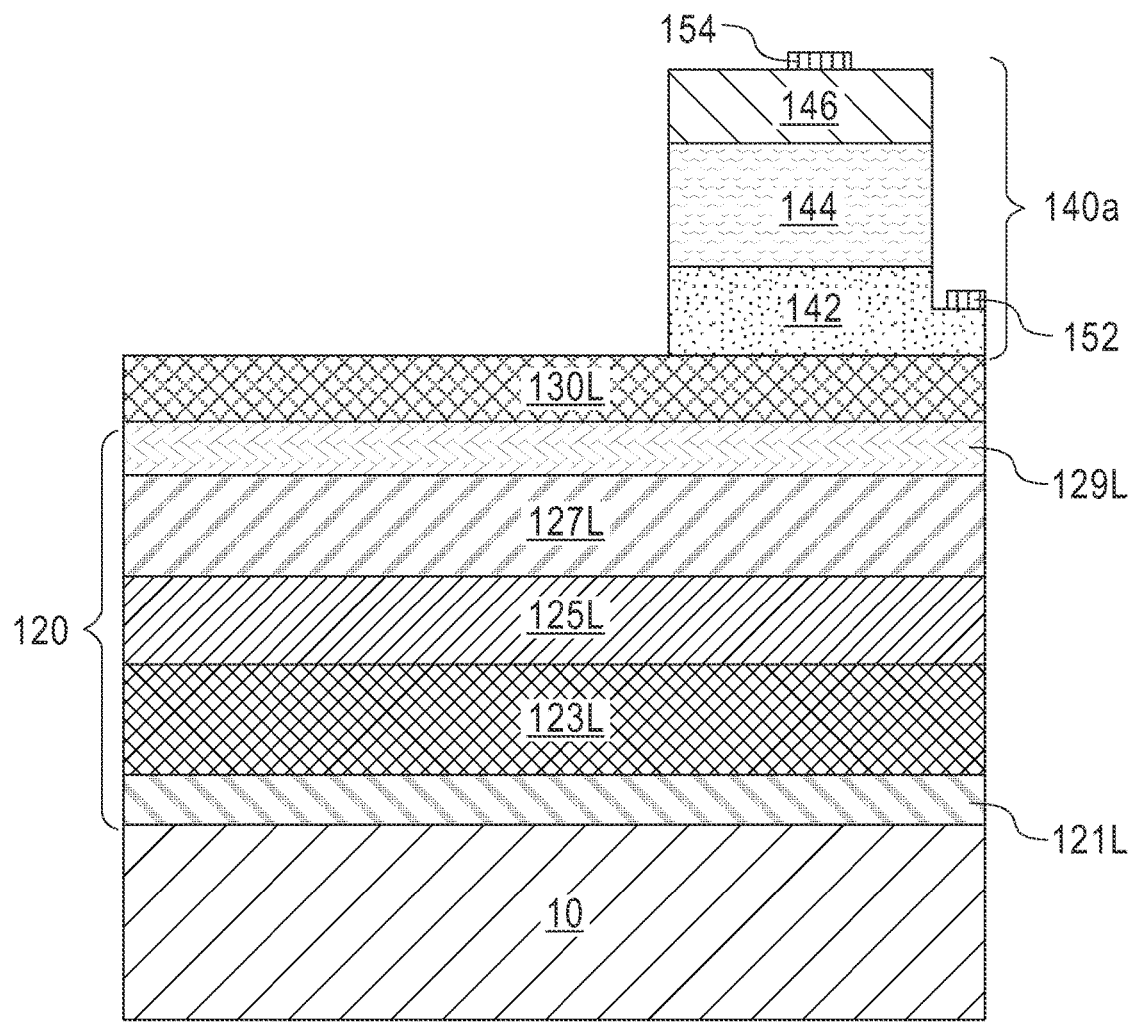
FIG. 9 a cross-sectional view of the second exemplary semiconductor structure of FIG. 8 after forming a photodetector over a portion of the first multilayer structure located in a first region of the substrate and forming contact structures that provide electrical connections to components of the photodetector.

Referring to FIG. 9, a photodetector 140a is formed over a portion of the first multilayer structure 120 located in a first region of the substrate 10 by patterning the second multilayer structure 140 utilizing conventional photolithography and etching techniques. A first photoresist layer (not shown) is applied over the topmost surface of the second multilayer structure 140 and lithographically patterned such that a patterned first photoresist layer covers a portion of the second multilayer structure 140 located in the first region of the substrate 10. The exposed portion of the second multilayer structure 140 is then removed by an anisotropic etch, which can be a dry etch (e.g., RIE) or a wet chemical etch. The patterning of the second multilayer structure 140 exposes a portion of the etch stop layer 30L. The patterned first photoresist layer is subsequently removed, for example, by ashing.

The remaining portion of the doped bottom semiconductor layer 142L is herein referred to a doped bottom semiconductor portion 142, the remaining portion of the light-absorbing layer 144L is herein referred to a light-absorbing portion 144, and the remaining portion of the doped top semiconductor layer 146L is herein referred to a doped top semiconductor portion 146. The doped bottom semiconductor portion 142, the light-absorbing portion 144 and the doped top semiconductor portion 146 together constitute the photodetector 140a.

Next, the doped top semiconductor portion 146, the light-absorbing portion 144 and an upper portion of the doped bottom semiconductor portion 142 are selectively etched to form a mesa structure, thus exposing an end portion of the doped bottom semiconductor portion 142. The mesa etching can be performed by applying and lithographically patterning a second photoresist layer that is formed over the etch stop layer 130L and the photodetector 140a and transferring the pattern in the second photoresist layer into the remaining portion of the second multilayer structure 140 by a second anisotropic etch. The second anisotropic etch can be a dry etch such as RIE or a wet chemical etch. The patterned second photoresist layer is subsequently removed, for example, by ashing.

Subsequently, a first contact structure 152 is formed contacting the doped bottom semiconductor portion 142 and a second contact structure 154 is formed contacting the doped top semiconductor portion 146 by performing processing steps described above in FIG. 3. The first contact structure 152 forms ohmic contact with the doped bottom semiconductor portion 142, while the second contact structure 154 forms ohmic contact with the doped top semiconductor portion 146.

Figure 10:
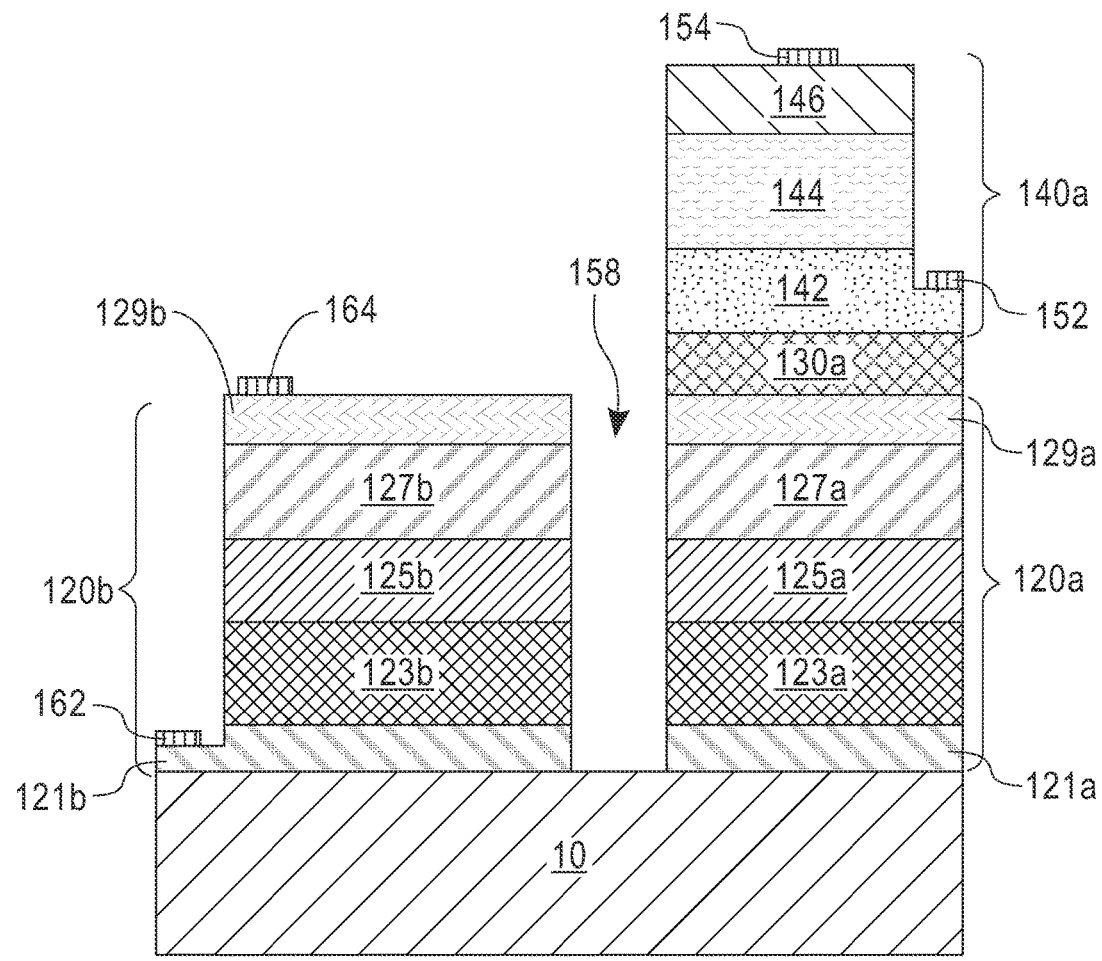
FIG. 10 is a cross-sectional view of the second exemplary semiconductor structure of FIG. 9 after forming a light source in a second region of the substrate and forming contact structures that provide electrical connections to components of the light source.

Referring to FIG. 10, a light source 120b is formed in a second region of the substrate 10 by patterning the first multilayer structure 120 utilizing conventional photolithography and etching techniques. A third photoresist layer (not shown) is applied over the etch stop layer 130L and the photodetector 140a and lithographically patterned to form an opening therein. The opening exposes a portion of the etch stop layer 130L and an underlying portion of the first multilayer structure 120 adjoined to the photodetector 140a. The pattern of the opening in the third photoresist layer is subsequently transferred into the etch stop layer 130L and the first multilayer structure 120 by a third anisotropic etch to form a trench 158 therein. The third anisotropic etch can be a dry etch such as RIE or a wet chemical etch. The patterned third photoresist layer is subsequently removed, for example, by ashing.

The trench 158 separates the first multilayer structure 120 into two parts. The first part of the first multilayer structure 120 is formed in the first region of the substrate 10 underneath the photodetector 140a and includes, from bottom to top, a first bottom contact portion 121a which is a remaining portion of the bottom contact layer 121L located in the first region of the substrate 10, a first bottom cladding portion 123a which is a remaining portion of the bottom cladding layer 123L located in the first region of the substrate 10, a first light-emitting portion 125a which is a remaining portion of the light-emitting layer 125L located in the first region of the substrate 10, a first top cladding portion 127a which is a remaining portion of the top cladding layer 127L located in the first region of the substrate 10 and a first top contact portion 129a which is a remaining portion of the top contact layer 129L located in the first region of the substrate 10. The second part of the first multilayer structure 120 is formed in the second region of the substrate 10 and includes, from bottom to top, a second bottom contact portion 121b which is a remaining portion of the bottom contact layer 121L located in the second region of the substrate 10, a second bottom cladding portion 123b which is a remaining portion of the bottom cladding layer 123L located in the second region of the substrate 10, a second light-emitting portion 125b which is a remaining portion of the light-emitting layer 125L located in the second region of the substrate 10, a second top cladding portion 127b which is a remaining portion of the top cladding layer 127L located in the second region of the substrate 10 and a second top contact portion 129b which is a remaining portion of the top contact layer 129L located in the second region of the substrate 10. The first part of the first multilayer structure 120 in the first region of the substrate 10 is a non-device part 120a over which the photodetector 140a is located. The second part of the first multilayer structure 120 in the second region of the substrate 10 constitutes the light source 120b. The trench 158 also separates the etch stop layer 130L into two portions. The first portion of the etch stop layer 130L is present between the photodetector 140a and the non-device part 120a of the first multilayer structure 120. The first portion of the etch stop layer 30L is herein referred to as the first etch stop portion 130a. In one embodiment, a sidewall of the first etch stop portion 130a is vertically coincident with sidewalls of the first doped bottom semiconductor portion 142, the first light-absorbing portion 144 and the first doped top semiconductor portion 146 in the photodetector 140a and sidewalls of the first bottom contact portion 121a, the first bottom cladding portion 123a, the first light-emitting portion 125a, the first top cladding portion 127a and the first top contact portion 129a in the non-device part 120a of the first multilayer structure 120. The second portion of the etch stop layer 30L is subsequently removed from the topmost surface of the light source 120a to exposed the second top contact portion 129b.

Next, the second top contact portion 129b, the second top cladding portion 127b, the second light-emitting portion 125b, the second bottom cladding portion 123b and an upper portion of the second bottom contact portion 121b are selectively etched to form a mesa structure, thus exposing an end portion of the second bottom contact portion 121b. The mesa etching can be performed by applying and lithographically patterning a fourth photoresist layer that is formed over the light source 120b, the photodetector 140a and the substrate 10 and transferring the pattern in the fourth photoresist layer through the second top contact portion 129b, the second top cladding portion 127b, the second light-emitting portion 125b and the second bottom cladding portion 123b and into the upper portion of the second bottom contact portion 121b by a fourth anisotropic etch. The fourth anisotropic etch can be a dry as such as, for example, RIE or a wet chemical etch. The patterned fourth photoresist layer is subsequently removed, for example, by ashing.

Subsequently, a third contact structure 162 is formed contacting the second bottom contact portion 121b and a fourth contact structure 164 is formed contacting the second top contact portion 129b by performing processing steps described above FIG. 2. The third contact structure 162 forms ohmic contact with the second bottom contact portion 121b, while the fourth contact structure 164 forms ohmic contact with the second top contact portion 129b.

Figure 11:
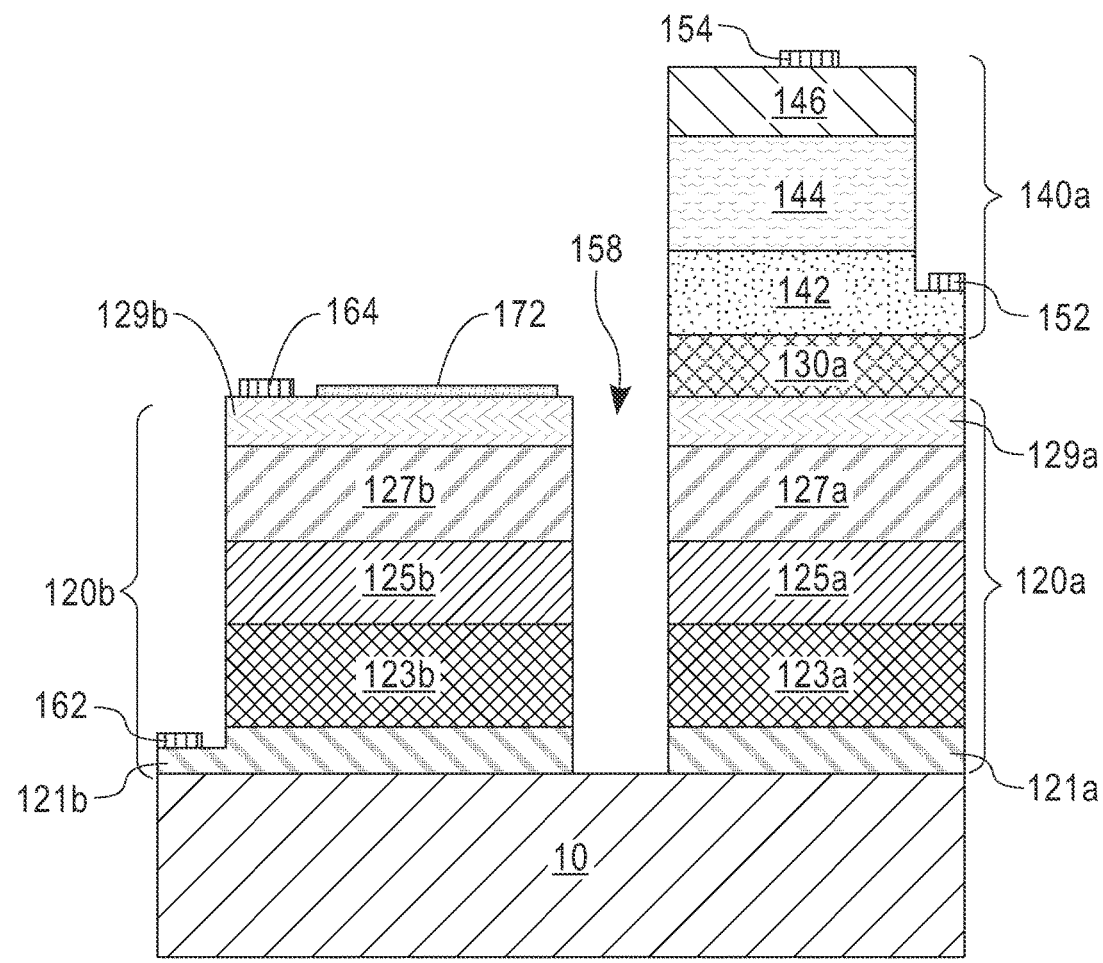
FIG. 11 is a cross-sectional view of the second exemplary semiconductor structure of FIG. 10 after forming a first optical filter on top of the light source.

Referring to FIG. 11, a first optical filter 172 is formed on a top surface of the second top contact portion 129b of the light source 120b. The first optical filter 172 may be an optical bandpass filter transmitting a specific wavelength range of light emitted from the light source 120b. The first filter 172 can have the same composition and thickness as the first optical filter 72 in the first embodiment, and can be formed by performing processing steps described above in FIG. 4.

Figure 12:
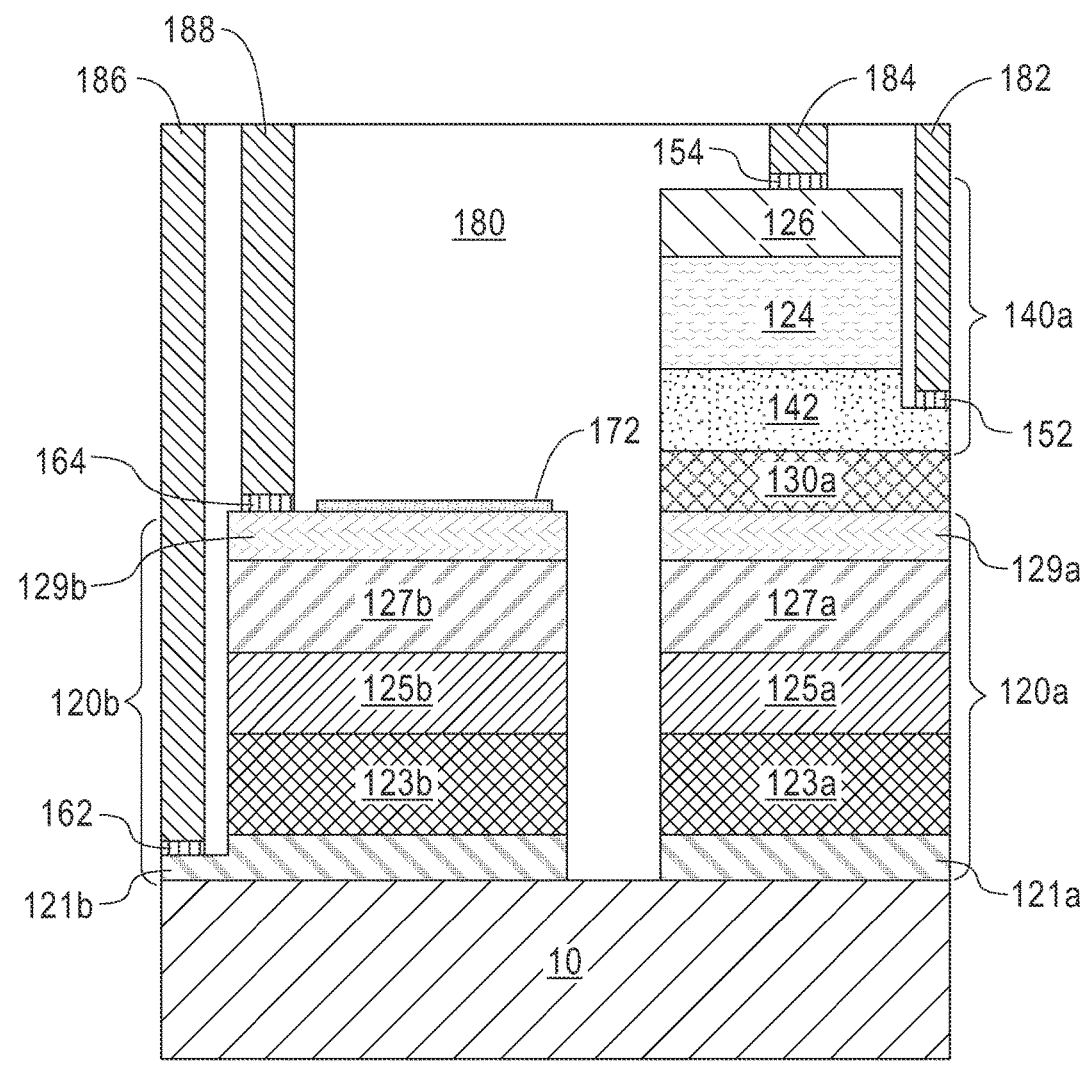
FIG. 12 is a cross-sectional view of the second exemplary semiconductor structure of FIG. 11 after forming an interlevel dielectric (ILD) layer over the light source, the photodetector and the substrate and forming interconnect structures electrically connected to contact structures in the light source and the photodetector.

Referring to FIG. 12, an ILD layer 180 is deposited to cover the light source 120b and the photodetector 140a and to completely fill the trench 158 by performing processing steps described above in FIG. 5.

Next, interconnect structures are formed extending through the ILD layer 180 by performing processing steps described above in FIG. 6. The interconnect structures include a first interconnect structure 182 in contact with the first contact structure 152, a second interconnect structure 184 in contact with the second contact structure 154, a third interconnect structure 186 in contact with the third contact structure 162 and a fourth interconnect structure 188 in contact with the fourth contact structure 164.

Figure 13:
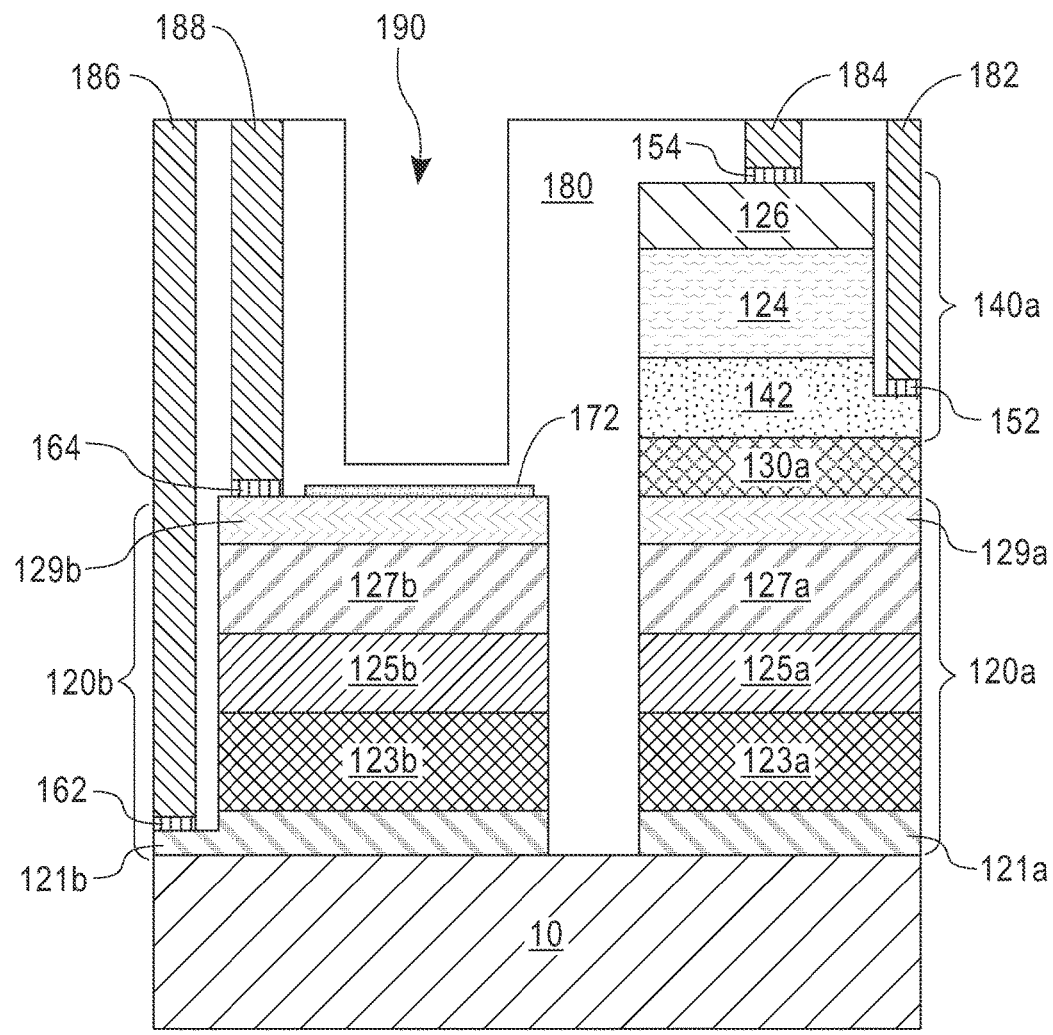
FIG. 13 is a cross-sectional view of the second exemplary semiconductor structure of FIG. 12 after forming a trench within the ILD layer.

Referring to FIG. 13, a second trench 190 that defines a microfluidic channel is formed within the ILD layer 180 by performing processing steps described above in FIG. 7. The second trench 190 is located above the first optical filter 172.

Figure 14:
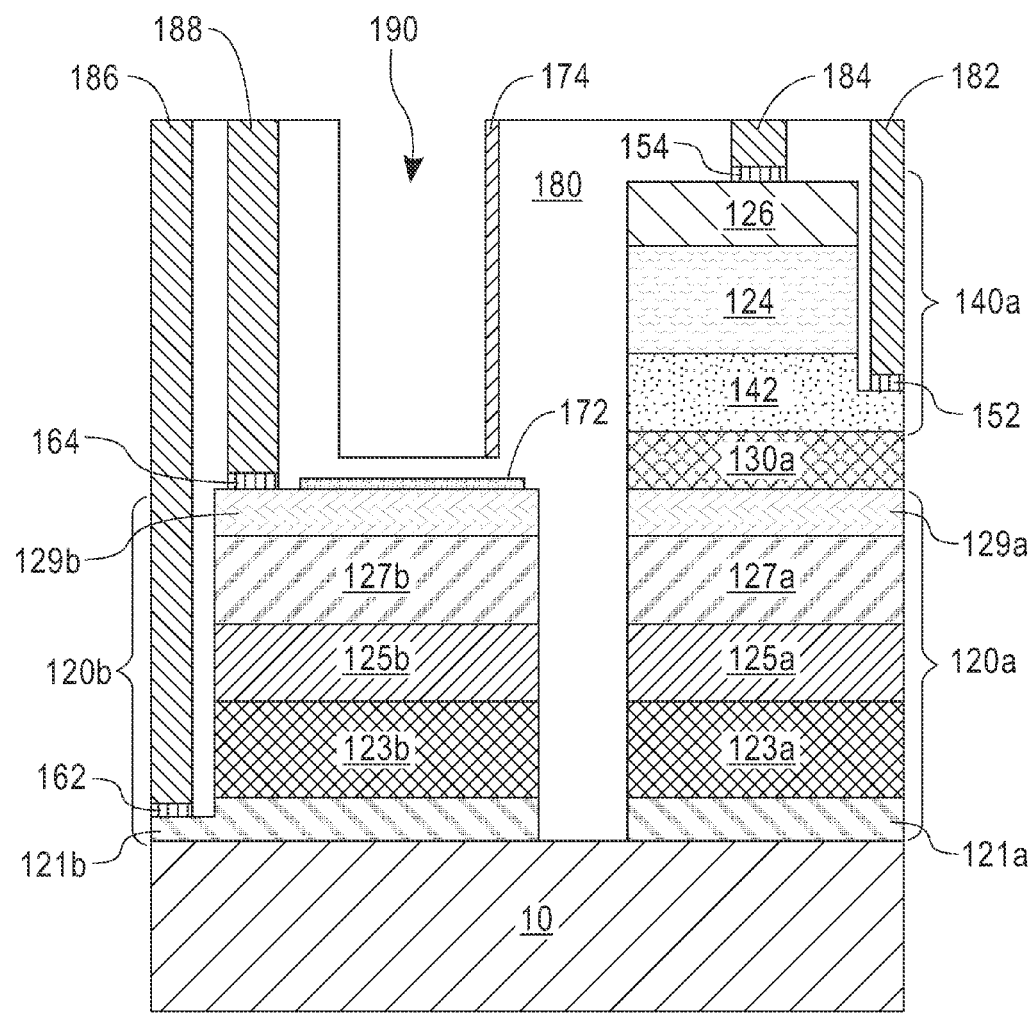
FIG. 14 is a cross-sectional view of the second exemplary semiconductor structure of FIG. 13 after forming a second optical filter on a sidewall of the trench proximal to an output facet of the light source.

Referring to FIG. 14, a second optical filter 174 is formed on a sidewall of the second trench 190 that is proximal to the photodetector 140a. The second filter 174 is generally transmissive except in the specific wavelength range of the excitation light emitted from the light source 120b. The second optical filter 174 can have the same composition and thickness as the second filter 74 in the first embodiment, and can be formed by performing processing steps described above in FIG. 4.

A second fluorescence on-chip sensor is thus formed by monolithically integrating a light source 120b which is a surface-emitting light source, a photodetector 140a and a microfluidic channel (i.e., second trench 190) on the same substrate 10. In the second embodiment of the present application, the photodetector 140a is located on one side of the microfluidic channel (i.e., second trench 190) that is located above the light source 120b. Thus, in the second embodiment, the light source 120b and the photodetector 140a are arranged orthogonally to each other. This orthogonal configuration prevents direct illumination of the photodetector 140a by the light source 120b, and thus the sensor sensitivity can be increased. During operation, the light emitted from the top surface of the light source 120b passes through the first optical filter 172 and illuminates the fluorescence materials in the analyte present in the microfluidic channel. The generated fluorescence light goes through the second optical filter 174 and into the photodetector 140a, which in turn generates an electrical signal in response. This electrical signal is indicative of the amount of target molecules present in the analyte.

Figure 15:
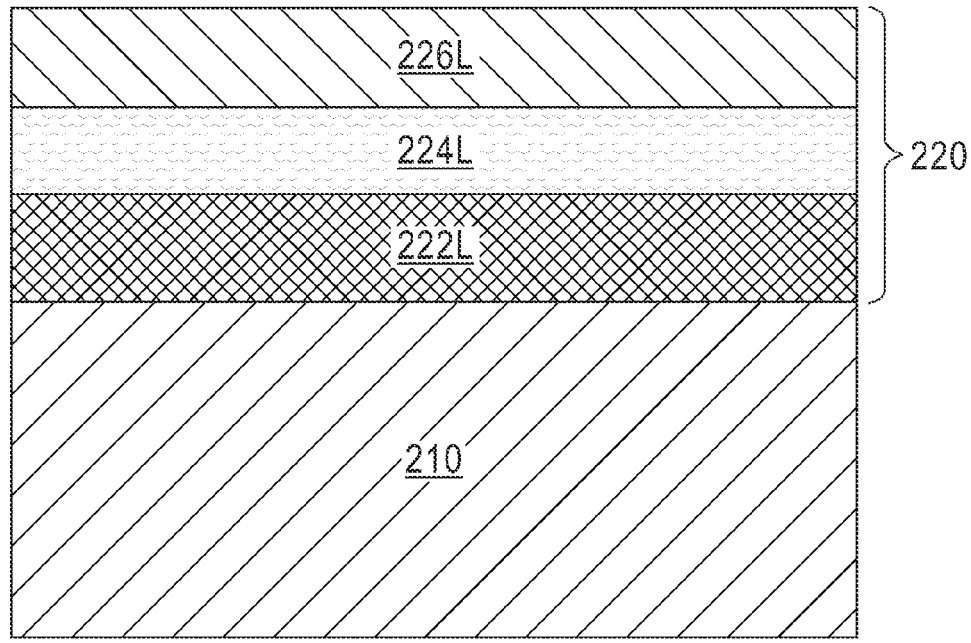
FIG. 15 is a cross-sectional view of a third exemplary semiconductor structure after forming a multilayer structure over a substrate according to a third embodiment of the present application.

Referring to FIG. 15, a third exemplary semiconductor structure of the present application according to a third embodiment of the present application includes a substrate 210 and a multilayer structure 220 formed thereon. The substrate 210 may include single crystalline silicon or polycrystalline silicon having a crystal orientation including, for example, {100}, {110} or {111}. The substrate 210 is doped with a dopant, which can be a p-type dopant such as, for example, boron (B) or aluminum (Al) or an n-type dopant such as, for example, phosphorus (P) or arsenic (As). In one embodiment, the substrate 210 is a p-type silicon substrate.

The multilayer structure 220 includes suitable semiconductor layers from which a light source can be formed. In one embodiment, the multilayer structure 220 may include, from bottom to top, a bottom cladding layer 222L, a light-emitting layer 224L and a top cladding layer 226L. The bottom cladding layer 222L, the light-emitting layer 224L and the top cladding layer 226L may be deposited utilizing an epitaxial growth (or deposition) process including MBE or MOCVD so that the substrate 210, the bottom cladding layer 222L, the light-emitting layer 224L and the top cladding layer 226L are epitaxially aligned among one another.

The bottom cladding layer 222L may include an n-doped III-V compound semiconductor material and may have a thickness ranging from 100 nm to 1 μm, although lesser and greater thicknesses can also be employed. In one embodiment, the bottom cladding layer 222L is composed of n-doped GaN.

The light-emitting layer 224L may include an III-V compound semiconductor material. In one embodiment, the light-emitting layer 224L may be formed with a single quantum well structure or a multi quantum well structure. In one embodiment, the light-emitting layer 224L comprises alternating layers of a quantum well layer formed of $In_xGa_{1-x}N$ with $0<x<1$ and a quantum barrier layer formed of GaN. The thickness of the light-emitting layer 224L may range from 100 nm to 1 μm, although lesser and greater thicknesses can also be employed.

The top cladding layer 226L may include a p-doped III-V compound semiconductor material and may have a thickness ranging from 100 nm to 1 μm, although lesser and greater thicknesses can also be employed. In one embodiment, the top cladding layer 226L is composed of p-doped GaN.

Figure 16:
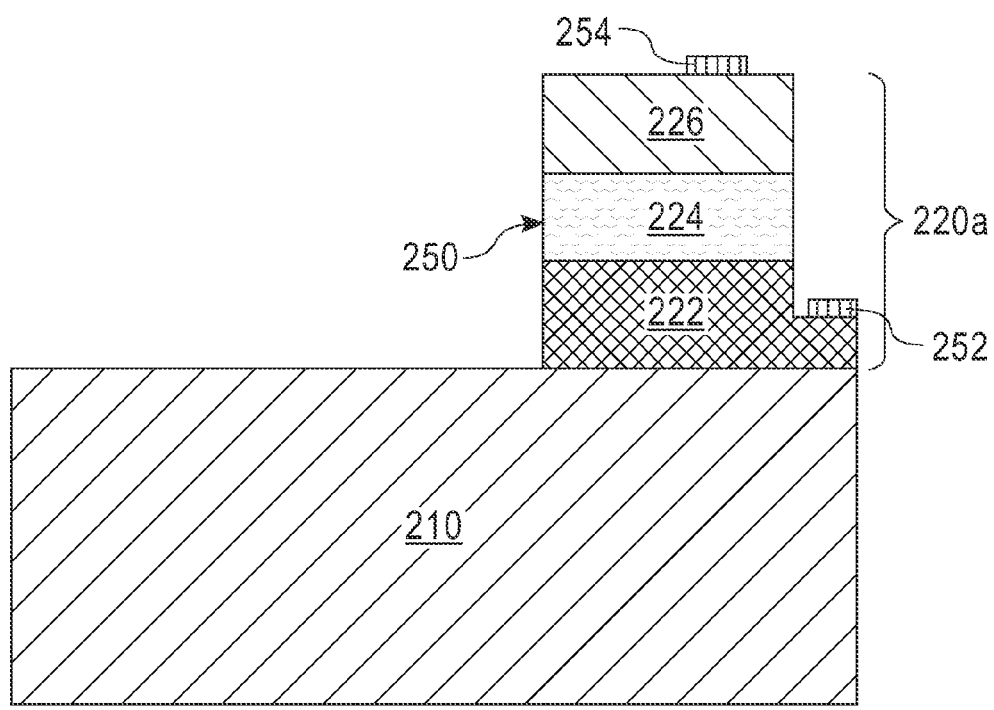
FIG. 16 a cross-sectional view of the third exemplary semiconductor structure of FIG. 15 after forming a light source in a first region of the substrate and forming contact structures that provide electrical connections to components of the light source.

Referring to FIG. 16, a light source 220a is formed in a first region of the substrate 210 by patterning the multilayer structure 220 utilizing conventional photolithography and etching techniques. A first photoresist layer (not shown) is applied over the topmost surface of the multilayer structure 220 and lithographically patterned such that a patterned first photoresist layer covers a portion of the multilayer structure 220 located in the first region of the substrate 210. The exposed portion of the multilayer structure 220 is then removed by an anisotropic etch, which can be a dry etch (e.g., RIE) or a wet chemical etch. The patterned first photoresist layer is subsequently removed, for example, by ashing.

The remaining portion of the bottom cladding layer 222L is herein referred to as a bottom cladding portion 222, the remaining portion of the light-emitting layer 224L is herein referred to as a light-emitting portion 224 and the remaining portion of the top cladding layer 226L is herein referred to as a top cladding portion 226. The bottom cladding portion 222, the light-emitting portion 224 and the top cladding portion 226 together constitute the light source 220a.

Next, the top cladding portion 226, the light-emitting portion 224 and an upper portion of bottom cladding portion 222 are selectively etched to form a mesa structure, thus exposing an end portion of the bottom cladding portion 222. The mesa etching can be performed by applying and lithographically patterning a second photoresist layer that is formed over the substrate 210 and the light source 220a and transferring the pattern in the second photoresist layer through the top cladding portion 226, the light-emitting portion 224 and into the upper portion of bottom cladding portion 222 by a second anisotropic etch. The second anisotropic etch can be a dry etch such as RIE or a wet chemical etch. The patterned second photoresist layer is subsequently removed, for example, by ashing.

Subsequently, a first contact structure 252 is formed contacting the bottom cladding portion 222 and a second contact structure 254 is formed contacting the top cladding portion 226 by performing processing steps described above in FIG. 3. The first contact structure 252 forms ohmic contact with the bottom cladding portion 222, while the second contact structure 254 forms ohmic contact with the top cladding portion 226.

Figure 17:
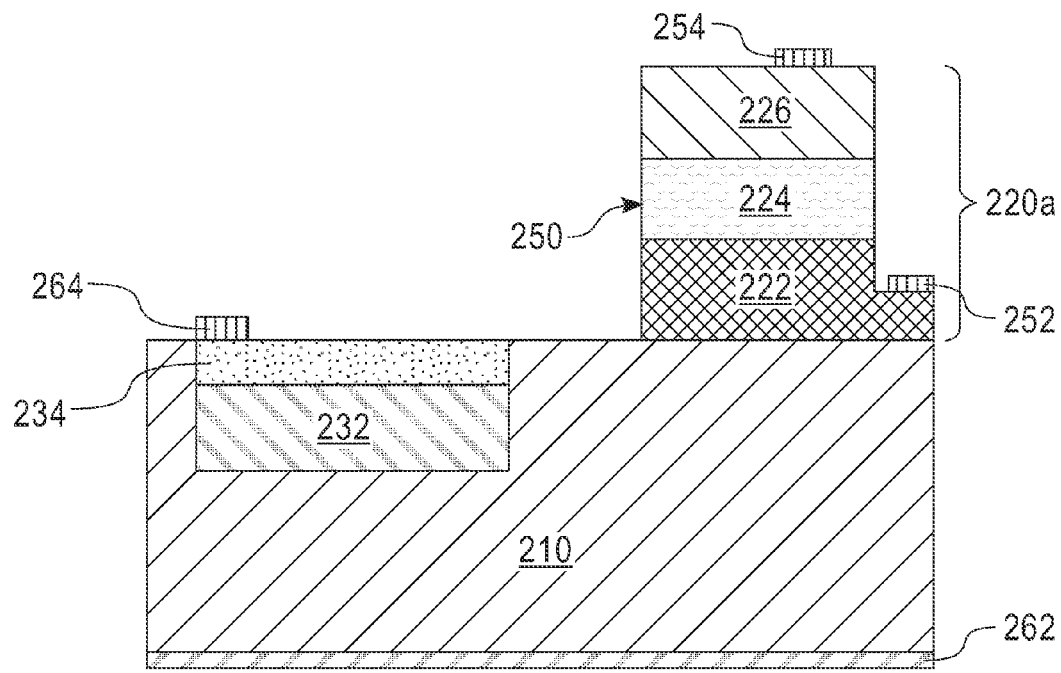
FIG. 17 is a cross-sectional view of the third exemplary semiconductor structure of FIG. 16 after forming a photodetector embedded within a second region of the substrate and forming contact structures that provide electrical connections to components of the photodetector.

Referring to FIG. 17, a photodetector is formed within a second region of the substrate 210. The photodetector includes a p-type substrate 210, an n-type lightly doped region 232 and an n-type heavily doped region 234. The n-type heavily doped region 234 is located in a top portion of the substrate 210 with a dopant concentration in the range of $1\times10^{18}$ atoms/cm$^3$ to $1\times10^{20}$ atoms/cm$^3$. The n-type lightly doped region 232 is located underneath the n-type heavily doped region 234. The dopant concentration of the n-type lightly doped region 232 is at least 10 times less than that of the n-type heavily doped region 234. The n-type lightly doped region 232 can be formed within the second region of the substrate 210 by a high energy ion implantation with energy levels, for example, on the order of 1 MeV. The n-type lightly doped region 232 thus formed is located at a greater depth in the substrate 210. Next, the n-type heavily doped region 234 can be formed above the n-type heavily doped region 232 by a low energy ion implantation with energy levels, for example, on the order of 500 KeV. The n-type heavily doped region 234 thus formed is located at a lesser depth in the substrate 210. The light source 220a and remaining portions of the substrate 210 are masked by a photoresist layer during the ion implantation processes in formation of the n-type lightly doped region 232 and the n-type heavily doped region 234. An activation anneal may be subsequently performed to activate the implanted dopants in the n-type lightly doped region 232 and the n-type heavily doped region 234.

Next, a third contact structure 262 is formed on a bottom surface of the substrate 210 opposite the light source 220a and a fourth contact structure 264 is formed on the n-type heavily doped region 234 by performing processing steps described above in FIG. 3. The third contact structure 262 forms ohmic contact with the p-type substrate 210, while the fourth contact structure 264 forms ohmic contact with the n-type heavily doped region 234. In one embodiment, the third contact 262 includes Pt/Ni/Au, and the fourth contact 264 includes Ti/Au.

Figure 18:
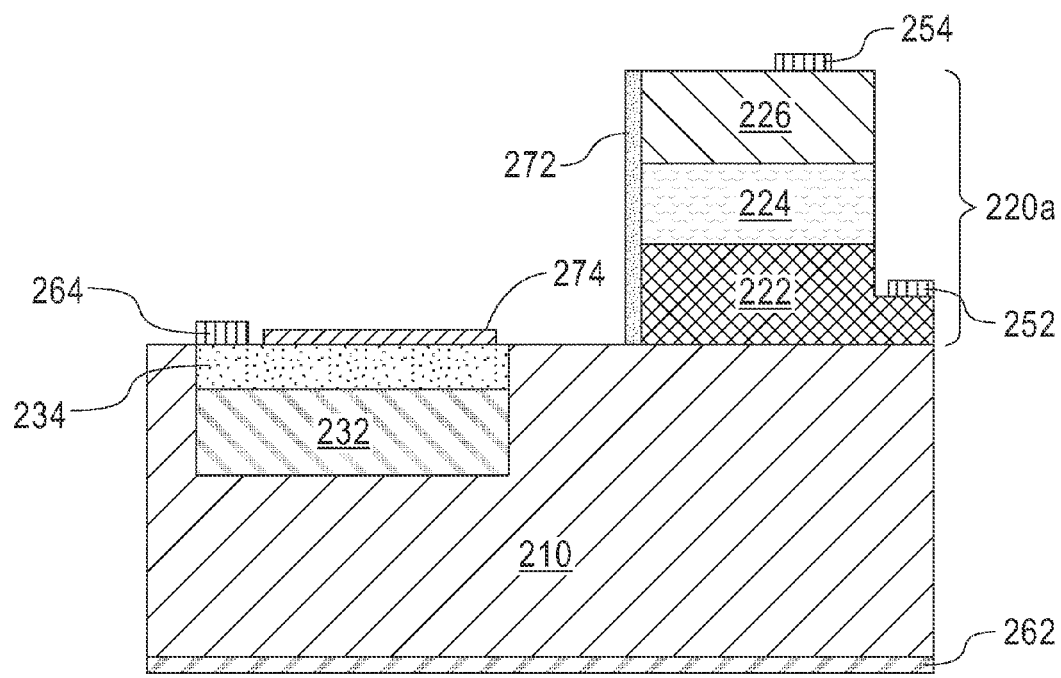
FIG. 18 is a cross-sectional view of the third exemplary semiconductor structure of FIG. 17 after forming a first optical filter on an output facet of the light source and forming a second optical filter on top of the photodetector.

Referring to FIG. 18, a first optical filter 272 is formed on the output facet of the light source 220a and a second optical filter 274 is formed on the top surface of the n-type heavily doped region 234 by performing processing steps described above in FIG. 4. The first optical filter 272 may be an optical bandpass filter transmitting a specific wavelength range of light emitted from the light source 220a. The first optical filter 272 may have the same composition as the first optical filter 72 in the first embodiment. The second optical filter 274 may be an optical bandpass filter and is generally transmissive except in the specific wavelength range of the excitation light emitted from the light source 220a. The second optical filter 274 may have the same composition as the second optical filter 74 in the first embodiment.

Figure 19:
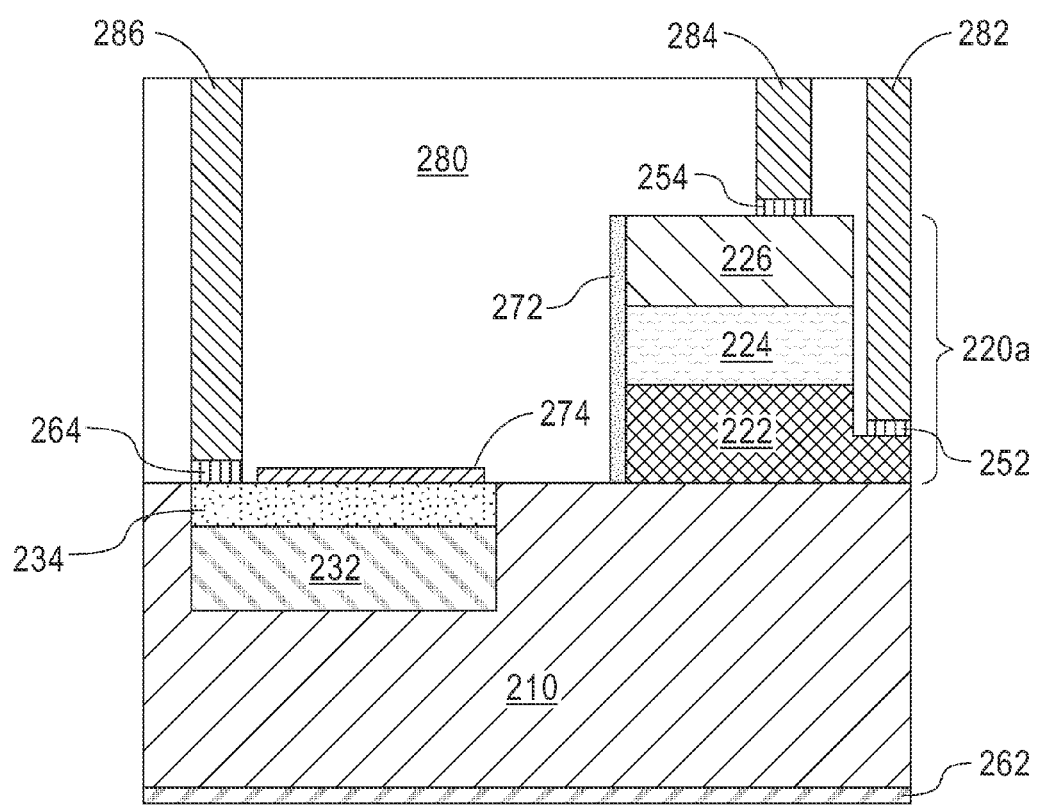
FIG. 19 is a cross-sectional view of the third exemplary semiconductor structure of FIG. 18 after forming an interlevel dielectric (ILD) layer over the light source, the photodetector and the substrate and forming interconnect structures electrically connected to contact structures in the light source and the photodetector.

Referring to FIG. 19, an ILD layer 280 is deposited to cover the light source 220a, the n-type heavily doped region 234 and the substrate 210 by performing processing steps described above in FIG. 5.

Next, interconnect structures are formed extending through the ILD layer 280 by performing processing steps of FIG. 6. The interconnect structures include a first interconnect structure 282 in contact with the first contact structure 252, a second interconnect structure 284 in contact with the second contact structure 254 and a third interconnect structure 286 in contact with the fourth contact structure 264.

Figure 20:
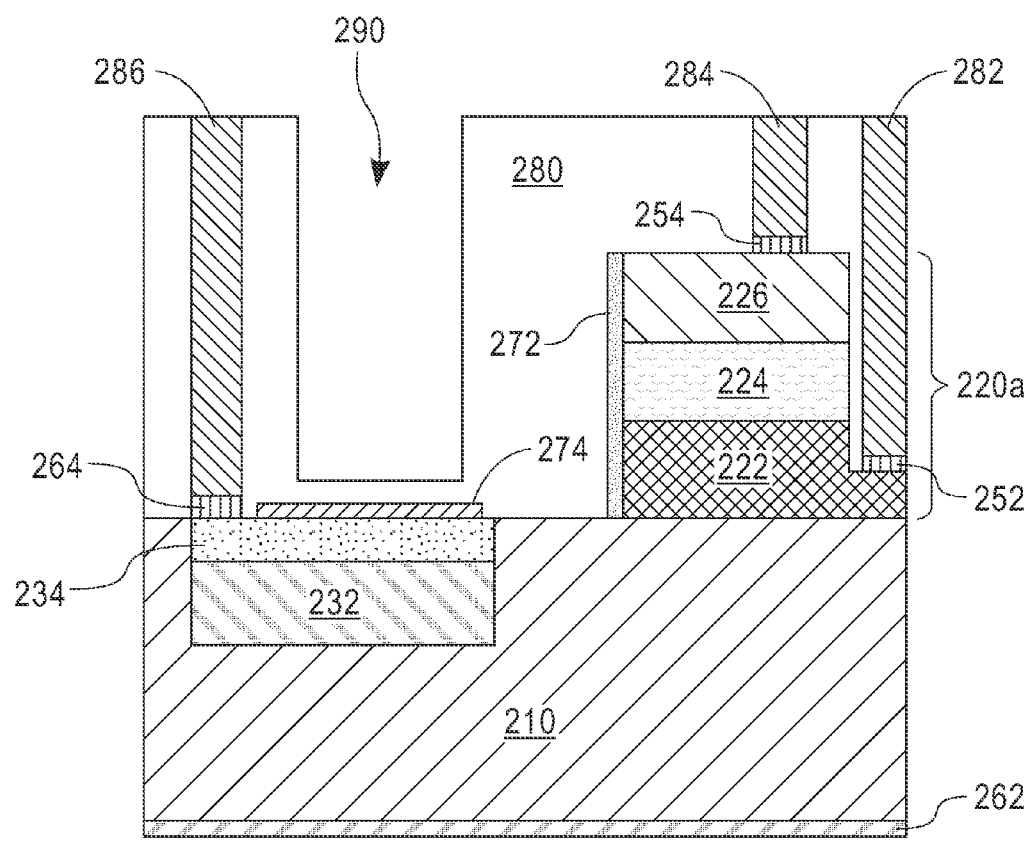
FIG. 20 is a cross-sectional view of the third exemplary semiconductor structure of FIG. 19 after forming a trench within the ILD layer.

Referring to FIG. 20, a trench 290 that defines a microfluidic channel is formed within the ILD layer 280 by performing processing steps described above in FIG. 7. The trench 290 is located above the second optical filter 274.

A third fluorescence on-chip sensor is thus formed by monolithically integrating a light source 220a which is an edge-emitting light source and a microfluidic channel (i.e., trench 290) on the same substrate 210 containing a photodetector (210, 232, 234) embedded therein. In the third embodiment of the present application, the photodetector (210 232, 234) is embedded within the substrate 210 over which the microfluidic channel (i.e., trench 290) is present. The light source 220a is located on one side of the microfluidic channel, thus is arranged orthogonally to the photodetector (210, 232, 234). This orthogonal configuration prevents direct illumination of the photodetector (210, 232, 234) by the light source 220a, and thus the sensor sensitivity can be increased. During operation, the light emitted from the output facet 250 of the light source 220a passes through the first optical filter 272 and illuminates the fluorescence materials in the analyte present in the microfluidic channel. The generated fluorescence light goes through the second optical filter 274 and into the photodetector (210, 232, 234), which in turn generates an electrical signal in response. This electrical signal is indicative of the amount of target molecules present in the analyte.

While the present application has been particularly shown and described with respect to preferred embodiments thereof, it will be understood by those skilled in the art that the foregoing and other changes in forms and details may be made without departing from the spirit and scope of the present application. It is therefore intended that the present application not be limited to the exact forms and details described and illustrated, but fall within the scope of the appended claims.

What is claimed is:

1. A monolithically integrated semiconductor structure comprising:
   a first semiconductor device located over a first part of a multilayer structure that is located over a first region of a substrate;
   a second semiconductor device comprising a second part of the multilayer structure located over a second region of the substrate, the second part of the multilayer structure separated from the first part of the multilayer structure by a space;
   an interlevel dielectric (ILD) layer located over the first semiconductor device, the second semiconductor device and the substrate and within the space between the first part of the multilayer structure and the second part of the multilayer structure; and
   a microfluidic channel located within the ILD layer, wherein the microfluidic channel is present above the second semiconductor device,
   wherein the first semiconductor device is a light source, and the second semiconductor device is a photodetector, and a first optical filter is located on an output facet of the light source and sidewalls of the first part of the multilayer structure.

2. The semiconductor structure of claim 1, wherein the microfluidic channel is optically coupled to the first semiconductor device and the second semiconductor device.

3. The semiconductor structure of claim 1, wherein the light source comprises, from bottom to top, a bottom contact portion, a bottom cladding portion, a light-emitting portion, a top cladding portion, and a top contact portion.

4. The semiconductor structure of claim 1, wherein the first part of the multilayer structure comprises, from bottom to top, a first portion of a doped bottom semiconductor layer, a first portion of a light-absorbing layer, and a first portion of a doped top semiconductor layer, and the second part of the multilayer structure comprises, from bottom to top, a second portion of the doped bottom semiconductor layer, a second portion of the light-absorbing layer, and a second portion of the doped top semiconductor layer, wherein the second part of the multilayer structure provides the photodetector.

5. The semiconductor structure of claim 1, further comprising a second optical filter located on a topmost surface of the photodetector, wherein the microfluidic channel is located above the second optical filter.

6. The semiconductor structure of claim 1, further comprising an etch stop portion located between the first semiconductor device and the first part of the multilayer structure.

7. A monolithically integrated semiconductor structure comprising:
   a first semiconductor device located over a first part of a multilayer structure that is located over a first region of a substrate;
   a second semiconductor device comprising a second part of the multilayer structure located over a second region of the substrate, the second part of the multilayer structure separated from the first part of the multilayer structure by a space;
   an interlevel dielectric (ILD) layer located over the first semiconductor device, the second semiconductor device and the substrate and within the space between the first part of the multilayer structure and the second part of the multilayer structure; and
   a microfluidic channel located within the ILD layer, wherein the microfluidic channel is present above the second semiconductor device,
   wherein the first semiconductor device is a photodetector, and the second semiconductor device is a light source, and a first optical filter located on a topmost surface of the light source, wherein the microfluidic channel is located above the first optical filter.

8. The semiconductor structure of claim 7, wherein the photodetector comprises, from bottom to top, a doped bottom semiconductor portion, a light-absorbing portion, and a doped top semiconductor.

9. The semiconductor structure of claim 7, wherein the first part of the multilayer structure comprises, from bottom to top, a first portion of a bottom contact layer, a first portion of a bottom cladding layer, a first portion of a light-emitting layer, a first portion of a top cladding layer, and a first portion of a top contact layer, and the second part of the multilayer structure comprises, from bottom to top, a second portion of the bottom contact layer, a second portion of the bottom cladding layer, a second portion of the light-emitting layer, a second portion of the top cladding layer, and a second portion of the top contact layer, wherein the second part of the multilayer structure provides the light source.

10. The semiconductor structure of claim 7, further comprising a second optical filter located on a sidewall of the fluidic channel that is most proximal to the photodetector.

* * * * *